(12) United States Patent
Timmer et al.

(10) Patent No.: US 12,350,747 B2
(45) Date of Patent: *Jul. 8, 2025

(54) INLINE SCANNING AND CUTTING ASSEMBLY AND METHOD OF OPERATION

(71) Applicant: Eagle Machinery & Supply, Inc., Sugarcreek, OH (US)

(72) Inventors: Andrew D. Timmer, Grand Haven, MI (US); Reuben R. Schlabach, Dundee, OH (US); Raymond A. Miller, Fresno, OH (US); Rudy A. Miller, Baltic, OH (US); Todd A. Spillman, Mineral City, OH (US); Kirk E. Spillman, Zoar, OH (US)

(73) Assignee: Eagle Machinery & Supply, Inc., Sugarcreek, OH (US)

( * ) Notice: Subject to any disclaimer, the term of this patent is extended or adjusted under 35 U.S.C. 154(b) by 317 days.

This patent is subject to a terminal disclaimer.

(21) Appl. No.: 18/050,065

(22) Filed: Oct. 27, 2022

(65) Prior Publication Data

US 2023/0136757 A1  May 4, 2023

Related U.S. Application Data

(60) Provisional application No. 63/273,590, filed on Oct. 29, 2021.

(51) Int. Cl.
   *B23D 59/00* (2006.01)
   *B27B 5/02* (2006.01)
   (Continued)

(52) U.S. Cl.
   CPC ......... *B23D 59/001* (2013.01); *B23D 59/006* (2013.01); *B27B 5/02* (2013.01);
   (Continued)

(58) Field of Classification Search
   CPC ...... G01N 23/04; G01N 23/083; G01N 23/18; G01N 33/46; G01N 21/95; G01N 2021/8411; G01N 2021/845; G01N 2223/619; G01N 2223/646; B27B 5/02; B27B 5/29; B23D 59/001
   See application file for complete search history.

(56) References Cited

U.S. PATENT DOCUMENTS 4,185,672 A * 1/1980 Vit .......................... B07C 5/14
                                                              83/160
4,301,844 A   11/1981 Tannerstal
                  (Continued)

*Primary Examiner* — Benjamin R Schmitt
(74) *Attorney, Agent, or Firm* — Sand, Sebolt & Wernow Co., LPA

(57) ABSTRACT

An automated inline rip saw system utilizing x-ray and optical scanning techniques to identify and detect flaws within a piece of wood. The present system may further utilize a precision skewing unit which may reduce or eliminate errors while allowing for precision rip cuts to be performed. Further, the present automated inline rip saw system may utilize multiple independently controlled saw blades to perform precision cuts. Finally, the present inline rip saw system may allow for more accurate detection of flaws or undesirable inclusions within the wood earlier in the wood production process, including the ability to scan for, identify, and remove sap wood from green lumber.

19 Claims, 33 Drawing Sheets

(51) Int. Cl.
  *B27B 5/29*    (2006.01)
  *B27B 5/34*    (2006.01)
  *G01N 23/04*   (2018.01)
  *G01N 23/083*  (2018.01)
  *G01N 23/18*   (2018.01)
  *G01N 33/46*   (2006.01)
  *B27H 3/02*    (2006.01)
  *G01N 21/84*   (2006.01)
  *G01N 21/95*   (2006.01)

(52) U.S. Cl.
  CPC ............... *B27B 5/29* (2013.01); *B27B 5/34* (2013.01); *G01N 23/04* (2013.01); *G01N 23/083* (2013.01); *G01N 23/18* (2013.01); *G01N 33/46* (2013.01); *B27H 3/02* (2013.01); *G01N 2021/8411* (2013.01); *G01N 2021/845* (2013.01); *G01N 21/95* (2013.01); *G01N 2223/619* (2013.01); *G01N 2223/646* (2013.01)

(56) References Cited

U.S. PATENT DOCUMENTS

| | | |
|---|---|---|
| 4,468,992 A | 9/1984 | McGeehee |
| 5,394,342 A * | 2/1995 | Poon ............ B27B 1/007 |
| | | 382/110 |
| 5,960,104 A | 9/1999 | Conners et al. |
| 6,597,761 B1 * | 7/2003 | Garms, III ......... B27B 1/007 |
| | | 378/58 |
| 6,624,883 B1 | 9/2003 | Zhou et al. |
| 6,666,246 B2 | 12/2003 | Gilbert |
| 10,406,613 B2 | 9/2019 | Wilkins et al. |
| 10,994,438 B2 | 5/2021 | Green et al. |
| 11,570,998 B2 | 2/2023 | Pfanstiel et al. |
| 2004/0057551 A1 * | 3/2004 | Skatter .............. G01N 33/46 |
| | | 378/54 |
| 2014/0251499 A1 | 9/2014 | Barker |
| 2020/0307014 A1 | 10/2020 | Spillman et al. |
| 2024/0300752 A1 | 9/2024 | Timmer et al. |

* cited by examiner

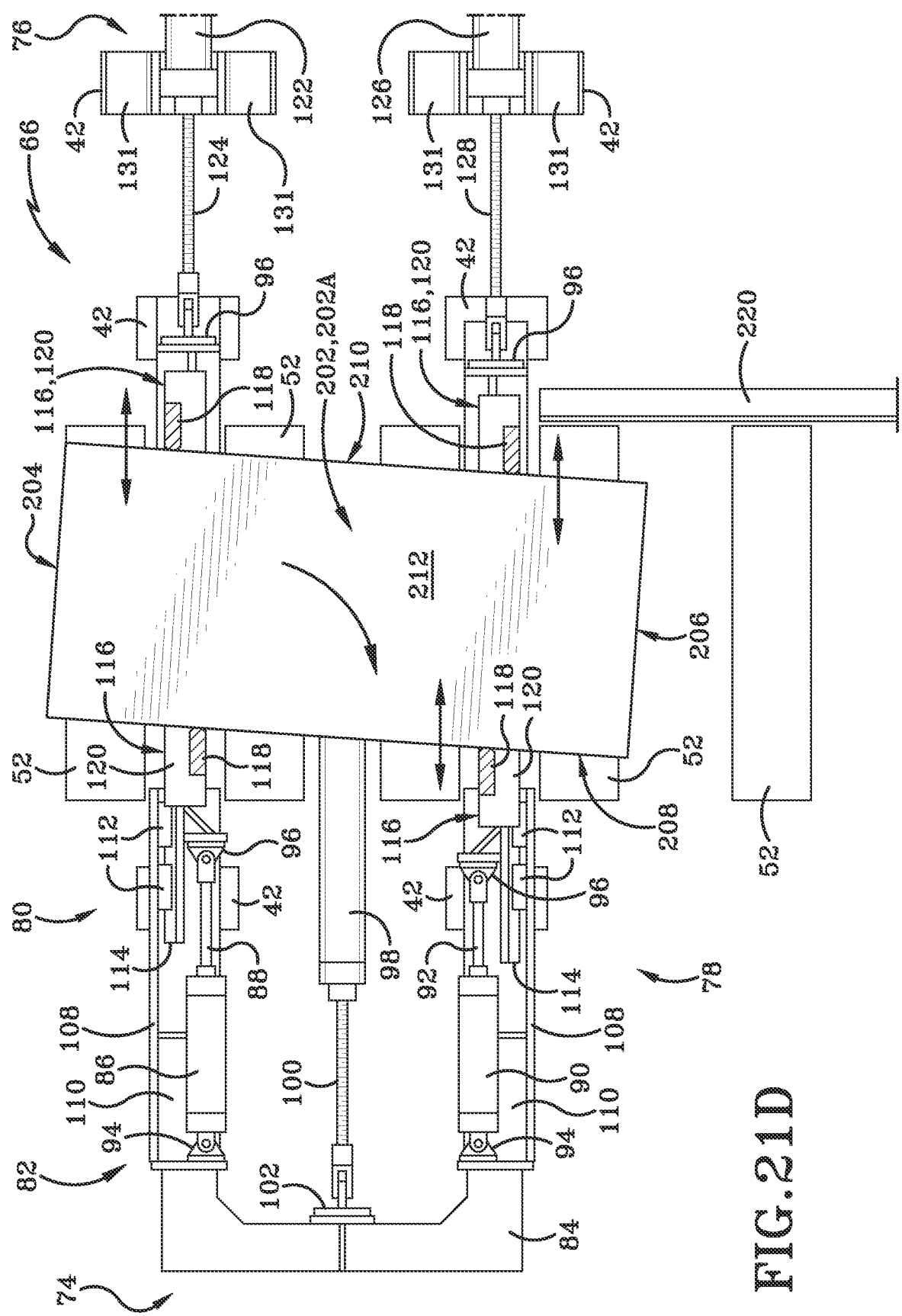

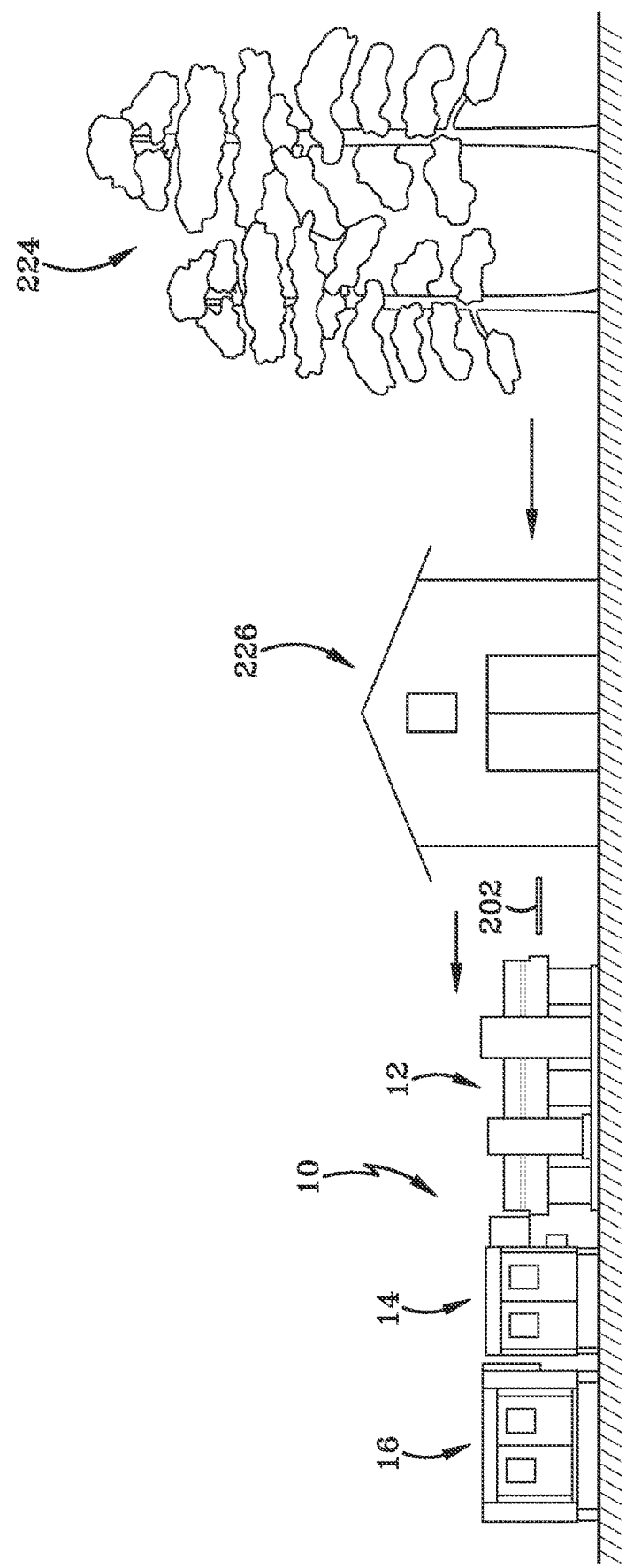

INLINE SCANNING AND CUTTING ASSEMBLY AND METHOD OF OPERATION

CROSS REFERENCE TO RELATED APPLICATIONS

This application claims the benefit of U.S. Provisional Application Ser. No. 63/273,590, filed on Oct. 29, 2021; the disclosure of which is incorporated herein by reference.

TECHNICAL FIELD

The present disclosure relates generally to the field of automated rip saws. More particularly, in one example, the present disclosure relates to an automated inline rip saw with a wood scanning system to optimize cuts in a piece of wood. Specifically, in another example, the present disclosure relates to an automated inline rip saw utilizing a dual scanning system and skewing device to optimize rip cuts in a particular piece of wood to remove defects or flaws and methods of use therefor. Further, the present disclosure relates to an automated inline rip saw system with the ability to detect, identify, and remove sap wood from green lumber.

BACKGROUND

Current automated inline rip saw systems generally are used to scan and remove defects from lumber in processing the wood for further applications. One particular industry where automated scanning and rip saw systems are commonly used is in the barrel stave industry wherein coopers, particularly those making barrels for producing alcohol for consumer consumption, tend to have strict requirements for the staves making up the barrel or cask used in the production of spirits. These requirements tend to relate to the length and/or width of the barrel staves and are further tied to the quality and/or density of the wood, as lower quality and less dense staves are prone to seepage or leakage when exposed to liquids for an extended period of time. Often, these barrels may be used to age spirits sometimes for periods extending over multiple years, therefore any leakage or seepage can be problematic.

Accordingly, current automated rip saw systems tend to scan lumber to be utilized in the production of staves for flaws such as cracks and/or for density variation in the wood which may indicate additional weak points or potential failure points.

Current systems tend to utilize x-rays and/or surface scans to seek such flaws before removing those flaws utilizing a rip saw. These rip saws tend to include multiple blades for variation in width and/or location of flaws to be removed. Further, current systems commonly utilize a skewer or skewing device to angle the wood to further enhance the removal of unwanted portions thereof.

Most commonly, current automated rip saw and scanning systems are typically employed towards the end of the processing cycle wherein the wood exiting the automated rip saw systems may then be processed and used for their intended purpose, for example, for forming barrels or casks when the wood product is stave wood.

Current systems, as they are employed later in the process, tend to be successful in scanning for surface variation and/or physical flaws such as knots, cracks, split sections of the wood and the like. Further, current systems may utilize x-rays to scan for density variation in an attempt to identify areas of lower density and remove the same. However, current systems are not typically adept at identifying areas of sap wood which are prone to leakage or seepage when utilized in barrel staves. Further, current systems cannot reliably detect wood rays which, if steeper than 45 degrees, can cause leakage and seepage, as well. Therefore, current systems tend to error on the side of over removal of suspect sections, resulting in less usable wood and more wood waste, further increasing the cost of such systems.

Additionally, current rip saw systems utilizing a skewer or skewing device typically employ skewing devices that are not precise and can sometimes result in portions of a board being removed when not intended or alternatively portions of the board intended to be removed being left with the end product. Neither situation is ideal as the former can increase cost and waste, while the latter can increase the number of flaws included in the end product.

Further, current rip saw systems typically employ multiple saw blades to perform specific tasks and/or provide multiple rip cuts in a single piece of wood. While these multiple blades are effective, it is most commonly found that a single motor may control multiple saw blades within a rip saw system which may be effective but may limit the ability of the saw system to make precision cuts and/or reduce the ability of the system to adjust to variations in the wood stock.

SUMMARY

The present disclosure addresses these and other issues by providing an automated inline rip saw system utilizing x-ray and optical scanning techniques to identify and detect flaws within a piece of wood. The present system may further utilize a precision skewing unit which may reduce or eliminate errors while allowing for precision rip cuts to be performed. Further, the present automated inline rip saw system may utilize multiple independently controlled saw blades to perform precision cuts. Finally, the present inline rip saw system may allow for more accurate detection of flaws or undesirable inclusions within the wood earlier in the wood production process, including the ability to scan for, identify, and remove sap wood from green lumber.

In one aspect, an exemplary embodiment of the present disclosure may provide an automated rip saw system comprising: a first scanner operable to scan a piece of wood with x-rays; a second scanner operable to optically scan the piece of wood; a skewing unit operable to skew the piece of wood; a cutting unit having at least one saw assembly therein operable to cut the piece of wood; and a continuous path defined through the first scanner, the second scanner, the skewing unit, and the cutting unit; wherein the piece of wood is skewed by the skewing unit to an angle relative to the path such that at least one saw assembly of the cutting unit is aligned with the piece of wood to remove one or more of a knot, a ray, and an area of sapwood detected by at least one of the first and second scanners.

In another aspect, an exemplary embodiment of the present disclosure may provide a method of cutting a piece of wood comprising: inserting a piece of wood into a first scanner of a rip saw system; performing an x-ray scan of the piece of wood with the first scanner; moving the piece of wood from the first scanner to a second scanner with at least one roller assembly; performing an optical scan of the piece of wood with the second scanner; detecting and identifying at least one flaw in the piece of wood; moving the piece of wood from the second scanner to a skewing unit; skewing the piece of wood relative to a path defined through the first scanner, the second scanner, and the skewing unit; moving the skewed piece of wood from the skewing unit to a cutting unit having at least one saw assembly therein; and cutting the piece of wood with the at least one saw assembly to remove the at least one flaw therefrom.

In yet another aspect, and exemplary embodiment of the present disclosure may provide an automated rip saw system comprising: a scanning unit operable to scan a piece of wood with at least one of an x-ray scanner and an optical scanner; a skewing unit operable to skew the piece of wood; a cutting unit having a saw assembly including a first saw blade with a first dedicated motor and a second saw blade with a second dedicated motor within the cutting unit; and a continuous path defined through the scanning unit, the skewing unit, and the cutting unit; wherein the saw assembly is operable to make a first cut in the piece of wood with the first saw blade and a second cut in the piece of wood with the second saw blade.

In yet another aspect, and exemplary embodiment of the present disclosure may provide a method of making multiple rip cuts in a piece of wood comprising: inserting a piece of wood into a scanning unit of a rip saw system; performing at least one of an x-ray scan and an optical scan of the piece of wood with at least one scanner of the scanning unit; identifying at least one flaw in the piece of wood based a result of the scanning of the piece of wood; skewing the piece of wood relative to a path defined through the rip saw system; cutting the piece of wood with at least one saw blade of a first saw assembly to remove at least a portion of the piece of wood; and cutting the piece of wood with at least one other saw blade of a second saw assembly after cutting the wood with the first saw assembly.

In yet another aspect, and exemplary embodiment of the present disclosure may provide a saw system comprising: a first scanner operable to scan a piece of wood with x-rays; a second scanner operable to optically scan the piece of wood, the first and second scanner defining a scanning unit operable to detect at least one flaw being at least one of a ray and an area of sapwood within the piece of wood; a skewing unit operable to skew the piece of wood; a cutting unit having at least one saw assembly including at least one saw blade with a dedicated motor in operable connection therewith; the scanning unit, the skewing unit, and the cutting unit defining a continuous path by which the piece of wood may move therethrough; wherein the piece of wood is skewed by the skewing unit to an angle relative to the path such that at least one saw assembly of the cutting unit is aligned with the piece of wood to remove at least one detected flaw from the piece of wood.

In yet another aspect, and exemplary embodiment of the present disclosure may provide a method of detecting and removing rays in a piece of wood comprising: scanning a piece of wood with an x-ray scanner to detect an internal grain pattern thereof; scanning the piece of wood with an optical scanner to detect a surface grain pattern thereof; comparing the internal and the surface grain patterns to locate one or more rays in the piece of wood; determine the angle of any located rays relative to a direction of the grain patterns in the piece of wood; skew the piece of wood with a skewing unit of a saw system to align the piece of wood with at least one saw assembly of the saw system; and cutting out any located rays angled at 45° or greater relative to the direction of the grain pattern with the at least one saw assembly.

In yet another aspect, and exemplary embodiment of the present disclosure may provide a method of detecting and removing sapwood in a piece of wood comprising: scanning a piece of green wood with an x-ray scanner to detect at least one density variation within the piece of wood; scanning the piece of green wood with an optical scanner; comparing an x-ray image from the x-ray scanner with an optical image from the optical scanner to locate at least one area of sapwood within the piece of wood; skew the piece of wood with a skewing unit of a saw system to align the piece of wood with at least one saw assembly of the saw system; and cutting out any detected areas of sapwood with the at least one saw assembly.

In yet another aspect, and exemplary embodiment of the present disclosure may provide a rip saw assembly comprising: a first dust hood at least partially enclosing a first saw blade therein; a second dust hood at least partially enclosing a second saw blade therein; a frame having at least one rail; a first mounting sled engaged with the at least one rail of the frame and carrying the first dust hood and saw blade thereon; and a second mounting sled engaged with the at least one rail of the frame and carrying the second dust hood and saw blade thereon; wherein the first and second dust hoods are vertically movable relative to the first and second saw blades.

BRIEF DESCRIPTION OF THE SEVERAL VIEWS OF THE DRAWINGS

Sample embodiments of the present disclosure are set forth in the following description, are shown in the drawings and are particularly and distinctly pointed out and set forth in the appended claims.

FIG. 21D is an operational view of a skewing assembly, according to one aspect of the present disclosure.

FIG. 25 is an exemplary operational view of an automated inline rip saw system, according to one aspect of the present disclosure.

Similar numbers refer to similar parts throughout the drawings.

DETAILED DESCRIPTION

Figure 1:
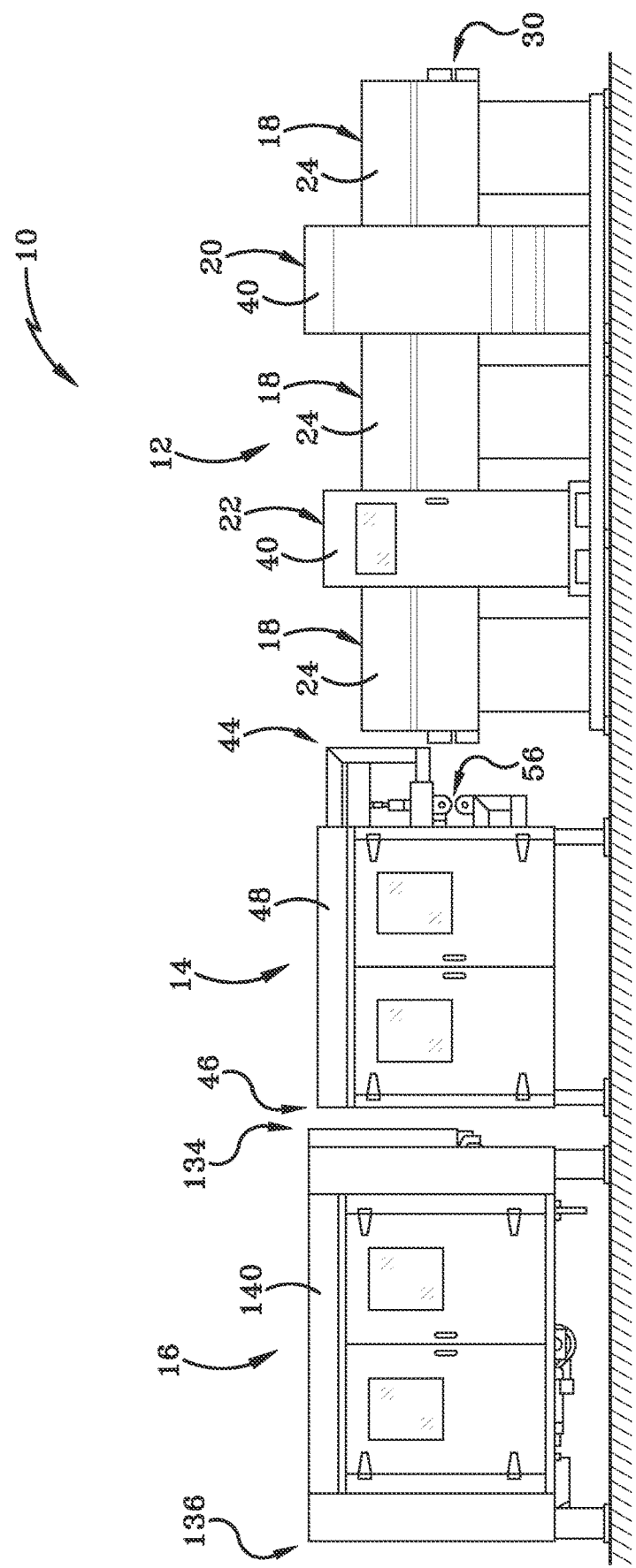
FIG. 1 is a front elevation view of an automated inline rip saw system, according to one aspect of the present disclosure.

With reference to the figures generally but with specific reference to FIG. 1, an automated inline rip saw system is shown and generally indicated at reference 10 and will be further referred to herein as rip saw system 10 or simply system 10. Rip saw system 10 may generally include three main sections, namely, a scanning unit 12, a skewing unit 14, and a cutting unit 16, each of which will be described in further detail below. As shown in the figures and discussed throughout, saw system 10 is oriented with scanning unit 12 to the right and cutting unit 16 to the left with skewing unit 14 therebetween; however, it will be understood that the relative position may be reversed as desired or as dictated by the desired implementation. For example, with reference to FIG. 1, the scanning unit 12 is depicted to the right of the skewing unit 14 but in practice, the scanning unit 12 may be on either the right or the left of the skewing unit 14. Similarly, the cutting unit 16 may be on either the right or the left of skewing unit 14 and opposite scanning unit 12. As contemplated and as discussed further herein, it is anticipated that wood will travel through saw system 10 by first encountering scanning unit 12, then into skewing unit 14, before ultimately reaching cutting unit 16.

Rip saw system 10 may be electrically controlled and may include appropriate electrical connections, including one or more power connections. Rip saw system 10 may also include any suitable connections to various external components, such as pneumatic connections, hydraulic connections, or any other required connections as dictated by the desired implementation. It will be understood that these connections may be made using industry standard materials suitable for the desired purpose. It will be further understood that these systems and/or connections may or may not be present in all units of rip saw system 10, or alternatively may or may not be present in rip saw system 10 at all, depending on the desired implementation. Therefore, these connections and the particulars of the associated systems therewith are omitted from further discussion herein for purposes of clarity and brevity in the disclosure.

Similarly, rip saw system 10 and the various components thereof may further include additional elements such as braces, flanges, mounting points, mounting brackets, structural members, linkages, pulleys, belts, electronic components, optical components, pneumatic components, hydraulic components, data connections, communications components, wiring, hoses, hardware, or the like that may be utilized to connect mount support and/or control rip saw system 10 and its components thereof. These additional elements and components may vary depending on the specific implementation parameters of rip saw system 10 and may be included or excluded, as necessary, to allow for the configuration and operation of saw system 10. It will be further understood that these components and elements are presumed present within saw system 10 unless specifically stated to the contrary, but are otherwise hereinafter excluded from discussion for purposes of brevity and clarity in the disclosure.

In addition to the elements and components mentioned above or the specific aspects of rip saw system 10 discussed further below, rip saw system 10 may further include a safety shut off system that may include one or more manual and/or automatic shut off and safety devices. The safety system is contemplated to be included anywhere on or within rip saw system 10 provided it does not interfere with other components thereof. Any such safety system may comport with industry standards and/or safety regulations and may be any suitable safety system, as dictated by the desired implementation. Accordingly, any safety system or systems present in rip saw system 10 will be understood to operate according to its expected function and may include any and all necessary parts to accomplish such operation unless specifically stated otherwise.

Figure 2:
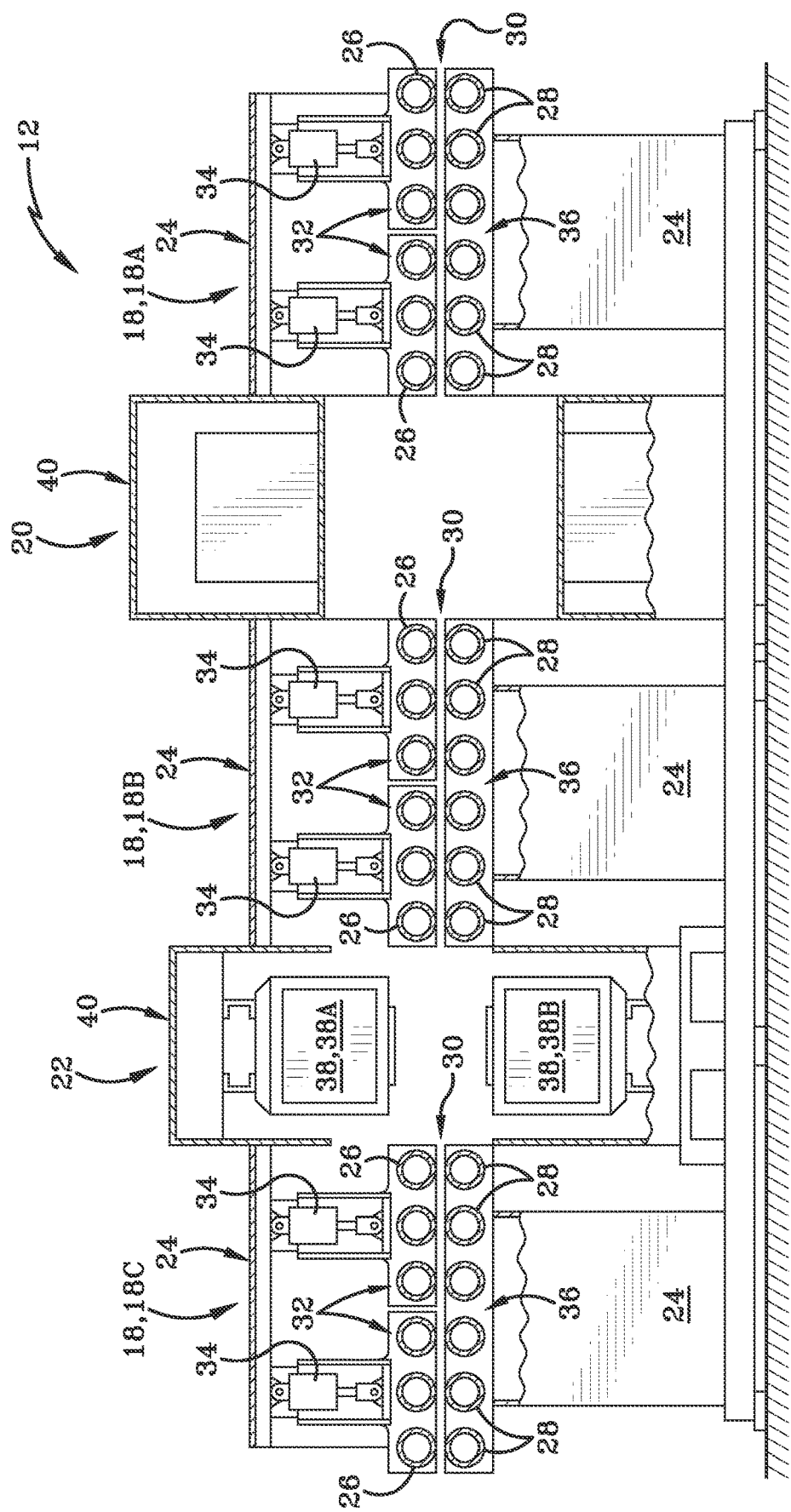
FIG. 2 is a front elevation partial cross section view of a scanning unit of an automated inline rip saw system, according to one aspect of the present disclosure.
Figure 3:
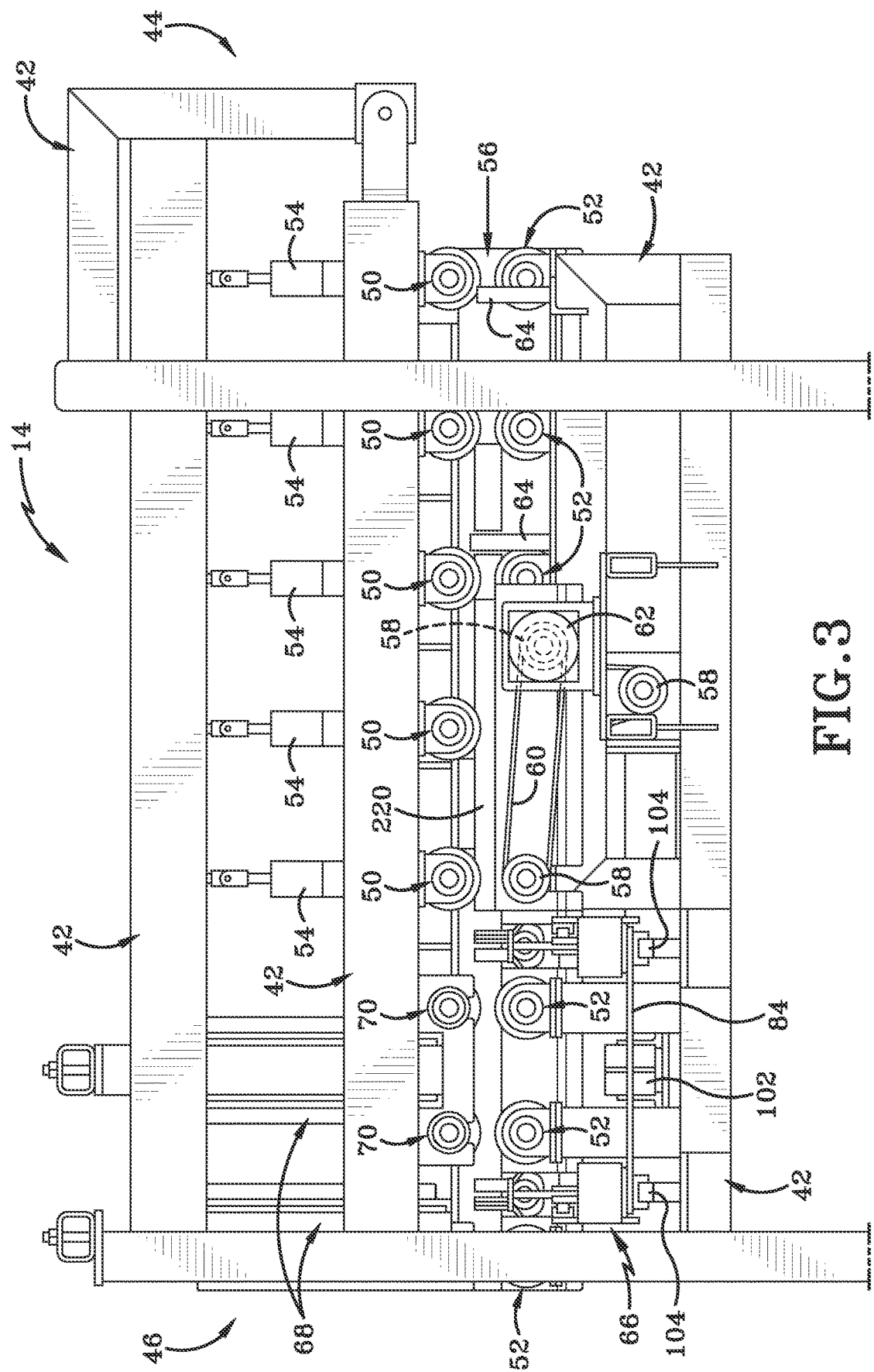
FIG. 3 is a front elevation view of a skewing unit of an automated inline rip saw system, according to one aspect of the present disclosure.
Figure 4:
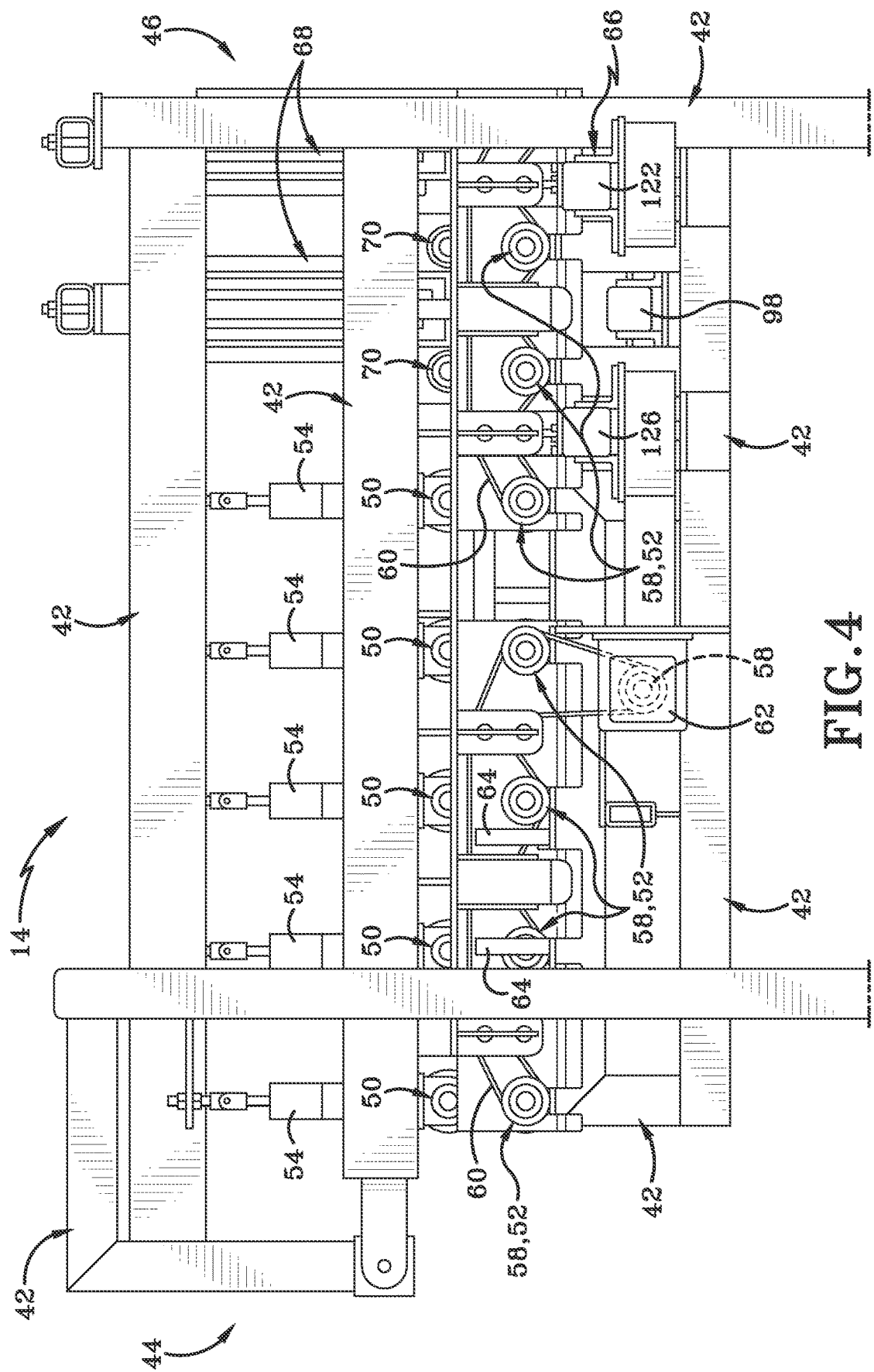
FIG. 4 is a rear elevation view of the skewing unit of an automated inline rip saw system, according to one aspect of the present disclosure.

With reference to FIGS. 1 and 2, scanning unit 12 may generally include one or more roller assemblies 18, a first scanner 20, and a second scanner. As depicted in FIGS. 1 and 2, scanning unit 12 is shown having three roller assemblies 18; however, it will be understood that any suitable number of roller assemblies 18 may be provided, as desired.

With reference to FIG. 2, roller assemblies 18 may generally be units operable to move a piece or pieces of wood through scanning unit 12, as discussed further below. Roller assemblies 18 may generally include a housing 24, which may enclose the elements and components of roller assembly 18 therein. Housing 24 of roller assemblies 18 may be constructed of any suitable material and may include one or more removable panels, viewing windows, access doors, or the like to allow an operator access to the components contained therein for maintenance, repair, or other similar activities. Housing 24 may further include any and all mounting hardware, fasteners, or the like as well as any necessary additional components including wiring switches or other similar such elements, as dictated by the desired implementation.

Roller assemblies 18 may further include one or more upper rollers 26 and one or more lower rollers 28, which may be in operable communication with suitable drive mechanisms such as servo motors or the like (not shown), as dictated by the desired implementation. Upper rollers 26 may be so named as they may be above lower rollers 28 and may interact with a top surface of a piece of wood moving through scanning unit 12, as discussed further herein.

A path 30 may be defined between upper and lower rollers 26, 28 and may generally be the path through scanning unit 12 (and may further form a portion of path 200 through system 10, as discussed below). Path 30 may be configured to accept a piece of wood therein, as discussed further below.

Upper rollers 26 may be arranged in groups or sets 32, which may be commonly controlled. For example, as shown in FIG. 2, groups of three upper rollers 26 may form an individual upper roller set 32. These sets may be commonly controlled in that each roller 26 within each upper roller set 32 may be operationally connected to the same control device and may operate in unison. Each upper roller set 32 may further include an actuator and piston assembly 34 which may serve to move upper rollers 26 vertically to accommodate pieces of wood of varying thickness. Actuator and piston assemblies 34 may further allow upper rollers 26 to interact with a top surface of a piece of wood as it moves down path 30 to prevent slipping or other such issues.

Lower rollers 28 may likewise be operationally connected into a lower roller set 36, which may be stationary relative to upper roller sets 32, or alternatively may be moveable relative thereto, as desired. Rollers 28 of lower roller set 36 may be operationally connected to a shared control unit, as desired, or may be alternatively connected to a plurality of drive units, as desired or as dictated by the desired implementation.

Upper and lower rollers 26 and 28 of roller assemblies 18 may be formed of any suitable material, including steel or other metals, polymers, plastics, or the like and may include a surface texture to aid in gripping or otherwise moving wood down path 30 in scanning unit 12. Rollers 26 and 28 may be mounted in a sufficient manner as to permit them to rotate about a longitudinal axis running through each individual roller 26, 28. Rollers 26, 28 may further include a projection, extension, flange, groove, channel, or similar feature to permit interaction between rollers 26, 28 and any drive components including drive belts or the like associated therewith and/or with any drive motor, as discussed further below.

Rollers 26 and 28 may be of any suitable size and rip saw system 10 may generally include multiple rollers of varying sizes depending upon their placement and/or function within rip saw system 10. As discussed further below, rollers in skewing unit 14 and cutting unit 16 may be substantially the same size and/or material as rollers 26 and 28 in roller assemblies 18 or may vary, as dictated by the desired implementation. According to another aspect, rollers throughout rip saw system 10 may vary within units or even within the same roller sets, as desired or dictated by the desired implementation. Rip saw system 10 may optionally include additional rollers that are not part of any particular roller set or unit. For example, rip saw system 10 may include exit rollers, guide rollers or the like. These additional rollers, where present, may be supplemental to the rollers discussed herein and may be freely spinning or may be included with or excluded from rip saw system 10, as needed or desired, to help facilitate movement of wood through the system 10.

As used herein, directional and positional terms, such as "ahead of" or "behind" will be understood to refer to the relative position of components based on when such components may be encountered by a piece of wood moving through rip saw system 10. Therefore, as best seen in FIG. 2 and according to one example, three roller assemblies 18 may be utilized with a first roller assembly 18A placed ahead of first scanner 20, a second roller assembly 18B may be positioned between first scanner 20 and second scanner 22, and a third roller assembly 18C may be placed behind second scanner 22 and ahead of skewing unit 14, as discussed further below.

First scanner 20, as mentioned above, may be an x-ray scanner or the like and may be operable to scan a piece of wood for various flaws, defects, and/or density variations therein. First scanner 20 may be any suitable size or shape and may be a commercially available x-ray scanning or other similar scanning device. According to one non-limiting example, first scanner 20 may be a WoodEye x-ray scanner available commercially from WoodEye AB (Sweden).

Where first scanner 20 is an x-ray scanner, it may be any suitable x-ray scanner or scanning device utilizing any suitable x-ray scanning protocol including traditional x-ray scans and/or backscatter x-ray detection, or the like. First scanner 20 may be further operable to switch between multiple x-ray techniques.

First scanner 20 may be placed within scanning unit 12 between a first roller assembly 18A and a second roller assembly 18B such that roller assemblies 18A and 18B may move a piece of wood through first scanner 20. First scanner 20 may omit any rollers or similar devices to move wood therethrough as those devices would be detected and/or present in any scan results and could therefore introduce error into the scanning results.

First scanner 20 may include a housing 40 which may be separate from housing 24 of roller assemblies 18. Alternatively, housing 40 of first scanner 20 may be continuous and form part of the same housing unit with roller assembly 18 housings 24. Similar to housing 24, housing 40 of first scanner 20 may include one or more removable panels, viewing windows, access doors, or the like to allow an operator access to the components contained therein for maintenance, repair, or other similar activities. Housing 40 may further include any and all mounting hardware, fasteners, or the like as well as any necessary additional components including wiring switches or other similar such elements, as dictated by the desired implementation.

Where first scanner 20 is an x-ray scanner, housing 40 thereof may further include or otherwise be constructed out of x-ray resistant material such as lead or the like. According to one aspect, housing 40 may be lined with an x-ray resistant material such as lead as to prevent x-rays from exiting housing 40 thereof. It is contemplated that housing 40 may only include x-ray impermeable material where the scanning device contained therein is an x-ray scanner. Where first scanner 20 is a scanner other than an x-ray scanner, housing may omit such x-ray impermeable materials.

First scanner 20 will be discussed and better understood through the operation and use thereof discussed further herein; however, it will be understood that first scanner 20 may be operated or otherwise used in a manner discussed below to identify specific defects and/or wood properties for removal from a piece of wood. First scanner 20 may be in communication with one or more computers or processors within the skewing unit 14 and/or cutting unit 16, as discussed further herein. Various other aspects and components of first scanner 20 may be discussed further below with the relation to the operation thereof.

Second scanner 22, as mentioned previously herein, may be an optical scanner or the like and may include one or more optical scanning devices 38. These optical scanning devices 38 may include an upper scanner 38A and a lower scanner 38B, which collectively may be operable to visualize both the top and bottom of a piece of wood. Optical scanning devices 38 may further include one or more side scanners (not shown) or other similar devices utilized to visualize the sides of a piece of wood moving through second scanner 22.

The optical scanning devices 38 may be commercially available high frame rate cameras, or any other suitable cameras, as dictated by the desired implementation. According to one aspect, optical scanning devices 38 may be WoodEye cameras available commercially from WoodEye AB (Sweden). According to another aspect, rip saw system 10 may further include additional optical scanning devices 38, as desired or dictated by the desired implementation.

As with first scanner 20, second scanner 22 may omit rollers or other similar devices to move wood through the scanner 22 as those structures would appear within the scanned images and may therefore introduce error therein. Accordingly, second scanner 22 may be located between two roller assemblies 18, such as second roller assembly 18B and third roller assembly 18C, for the effective transfer of wood therethrough, as discussed further herein.

First and second scanners 20 and 22 may have an open area defined in the middle thereof which may correspond to path 30 through scanning unit 12, which may allow free passage of wood therethrough. For purposes of scanning, it is contemplated that this open area between or within first and second scanners 20 and 22 may be sized such that at least one end of a piece of wood may be in contact with at least upper and/or lower rollers 26 and 28 of adjacent roller assemblies 18 as to prevent wood from falling into first and second scanners 20 and 22. Accordingly, first and second scanners 20 and 22 may further include additional supports or other similar structures (not shown) that are not within the scanning zone of first and second scanners 20 and 22 but may further support wood as it moves along path 30 through scanning unit 12. These additional structures may be included as necessary or as desired or dictated by the desired implementation.

As with first scanner 20, second scanner 22 may further include or may otherwise be enclosed within a housing 40 which may likewise be separate from housing 24 of roller assemblies 18. Alternatively, housing 40 of second scanner 22 may be continuous and form part of the same housing unit with scanner housings 40 and roller assembly 18 housings 24. Similar to housing 40 of the first scanner 20, housing 40 of second scanner 22 may include one or more removable panels, viewing windows, access doors, or the like to allow an operator access to the components contained therein for maintenance, repair, or other similar activities. Housing 40 may further include any and all mounting hardware, fasteners, or the like as well as any necessary additional components including wiring switches or other similar such elements, as dictated by the desired implementation.

Although shown in FIGS. 1 and 2 with the first scanner 20 (being the x-ray scanner) ahead of second scanner 22 (being the optical scanner), it will be understood that first and second scanners 20 and 22 may be provided in any suitable order and may similarly perform their respective scanning operations in any suitable order, as desired. For example, a piece of wood moving down path 30 through scanning unit 12, as depicted in FIGS. 1 and 2, would first encounter first scanner 20 and may be x-rayed before being moved through second scanner 22 for optical scanning. Alternatively, a piece of wood moving down path 30 may encounter an optical scanner first and then may be transferred through an x-ray scanner second.

First scanner 20 and/or second scanner 22 may further include other types of scanning devices and/or scanning sensors such as laser scanning devices or the like to supplement the scanning abilities of first and/or second scanner 20, 22. Laser scanning devices (not shown) may be any suitable laser types and may further include a laser generator and/or a receiver optic that are operable to produce a suitable laser to detect surface variations on the wood as it moves down path 30 through scanning unit 12. Any such scanning lasers included with scanners 20 and 22 may be in any suitable position and may be adjustable in position, angle, wavelength, and or type as dictated by the desired implementation.

Scanning unit 12, including roller assemblies 18, first scanner 20, and/or second scanner 22 may further include any other suitable sensors (such as sensors 64, discussed below) for the detection of the presence of wood therein. It is contemplated that sensors may be included to allow scanning unit 12 (and rip saw system 10 generally) to be automated to perform the desired functions and/or move wood therethrough based on the detection of the presence of a piece of wood, as discussed further below.

With reference to FIGS. 3-8, skewing unit 14 is shown and will now be described in more detail. Skewing unit 14 may generally have a frame 42, having a first end 44 defined as the end adjacent to or oriented towards scanning unit 12, and a second end 46 longitudinally opposite therefrom. Skewing unit 14 may be operationally connected to, or in operational contact with, scanning unit 12 (and cutting unit 16, discussed below) or may be placed adjacent to or in close proximity thereto, as dictated by the desired implementation.

Frame 42 may generally be a support frame which may include any suitable connections, mounts, brackets, supports, or the like to carry or otherwise connect to the various components of skewing unit 14 and will be understood to further include any necessary mounting surfaces, hardware, and the like, as well as all necessary or desired components for the proper operation thereof. For example, frame 42 may support each element of skewing unit 14 and may further support electrical wiring, electrical systems, and the like, as desired.

Skewing unit 14 may be fully or partially enclosed in a housing 48 (as best seen in FIG. 1 but removed in whole or in part in FIGS. 3-8 for clarity). Housing 48 may be constructed of any suitable material and may include one or more removable panels, viewing windows, access doors, or the like to allow an operator access to the components contained therein for maintenance, repair, or other similar activities. Housing 40 may further include any and all mounting hardware, fasteners, or the like as well as any necessary additional components including wiring switches or other similar such elements, as dictated by the desired implementation.

Skewing unit 14 may include a plurality of upper rollers 50, which may be substantially similar to upper rollers 26 of scanning unit 12 but for their location and function within skewing unit 14, as discussed further herein. Skewing unit 14 may further include a plurality of lower rollers 52, which likewise may be substantially similar to lower rollers 28 of scanning unit 12 but for their placement and function within skewing unit 14, as discussed further herein. As with upper rollers 26, upper rollers 50 of skewing unit 14 may be vertically movable utilizing one or more actuator and piston assemblies 54, which may allow upper rollers 50 to adjust to permit wood of varying thickness to be processed through skewing unit 14, as discussed further herein. According to one aspect, upper rollers 50 may be arranged in one or more sets, similar to roller sets 32, and may be moved as a single unit, or as smaller units having more than one roller 50 therein.

Upper rollers 50 may be non-powered rollers in that they may roll via contact with a piece of wood moving down a path 56 (which, along with path 30, may further form a portion of path 200 through system 10, as discussed below) defined through skewing unit 14 between upper rollers 50 and lower rollers 52. Alternatively, as desired, upper rollers 50 may be powered through any suitable or desired means including servo motors or the like.

Both upper and lower rollers 50 and 52 (and skewing rollers 70, discussed below) may be formed of any suitable material, including steel or other metals, polymers, plastics, or the like and may include a surface texture to aid in gripping or otherwise moving wood down path 56 in skewing unit 14. Rollers 50 and 52 may be mounted in a sufficient manner as to permit them to rotate about a longitudinal axis running through each individual roller 50, 52. Rollers 50, 52 may further include a projection, extension, flange, groove, channel, or similar feature to permit interaction between rollers 50, 52 and any drive components including drive belts 60 or the like associated therewith and/or with any drive motor 62, as discussed further below.

Lower rollers 52 may correspond to upper rollers 50 and may be considered powered rollers in that they may include one or more drive rollers 58 and one or more drive belts 60, which may be operable to connect rollers 52 to a drive motor 62. Drive motor 62 may be any suitable motor, including but not limited to servo motors or the like. Drive motor 62 may operable to power drive rollers 58 and belts 60 which in turn may further drive lower rollers 52.

Lower rollers 52 may be operationally connected in that they may all be driven via the same motor 62 and may therefore rotate in unison. Alternatively, one or more lower rollers 52 may have separate dedicated motors 62 to allow multiple modes of operation, as dictated by the desired implementation and discussed further herein.

Skewing unit 14 may further include one or more additional sensors 64, which may detect the presence, placement, and/or orientation of a piece of wood moving down path 56, as discussed further herein. Sensors 64 may be any suitable sensors including optical sensors, laser sensors, mechanical sensors, magnetic sensors, or the like, or any suitable combination thereof, as desired.

Figure 5:
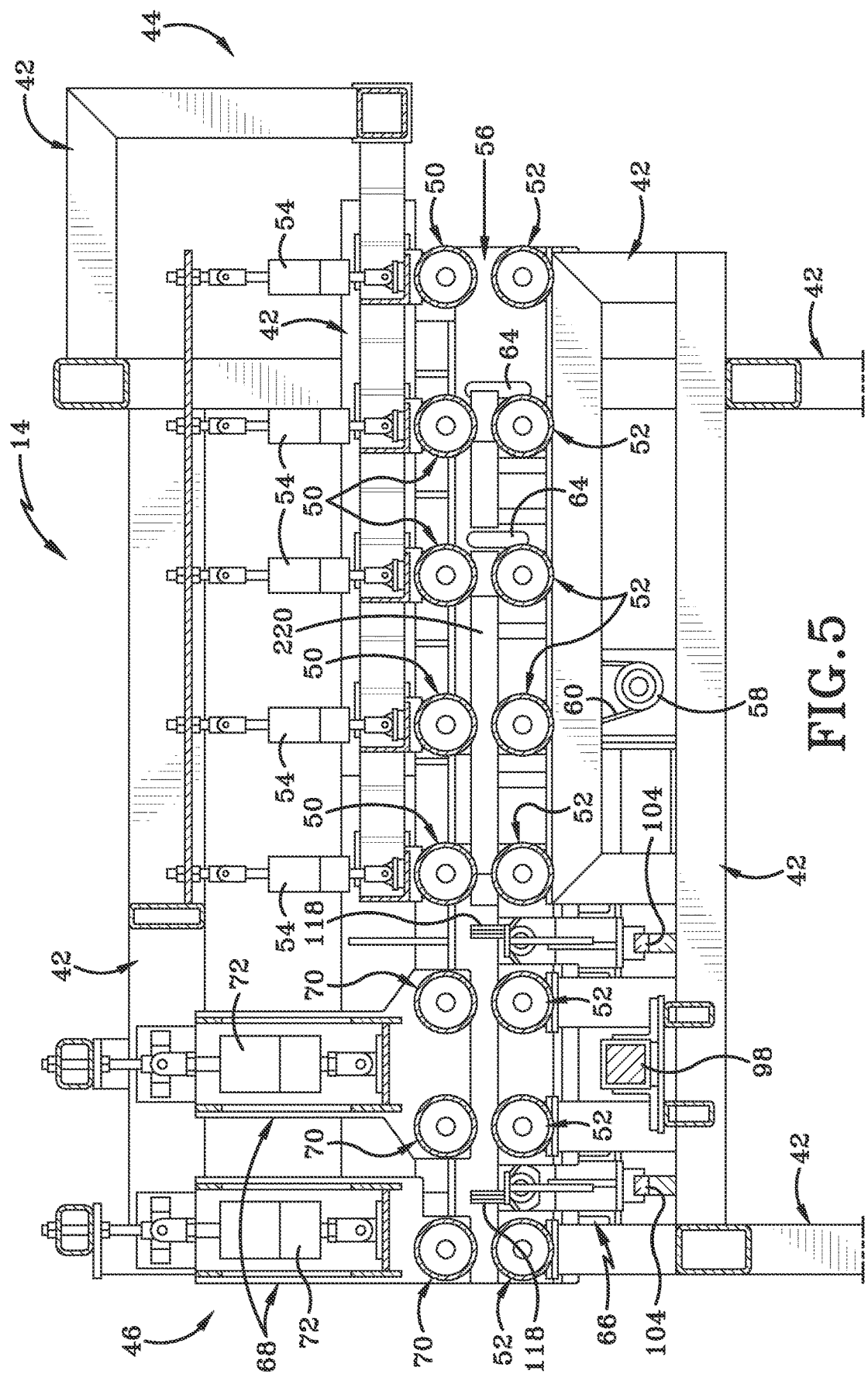
FIG. 5 is a front elevation cross section view of the skewing unit of an automated inline rip saw system, according to one aspect of the present disclosure.
Figure 6:
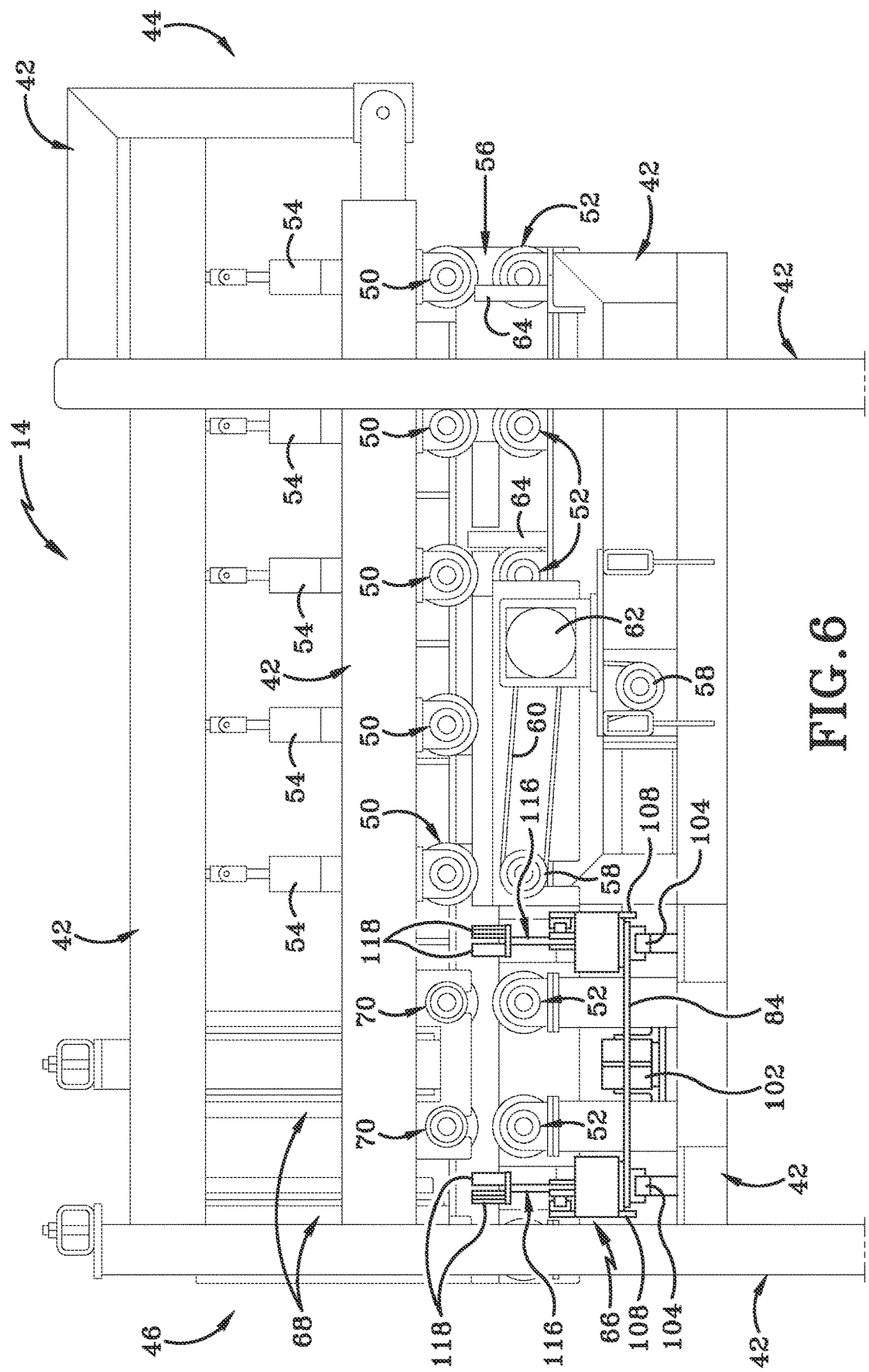
FIG. 6 is a front elevation view of the skewing unit of FIG. 3 with the skewing mechanism distinguished therein, according to one aspect of the present disclosure.
Figure 7:
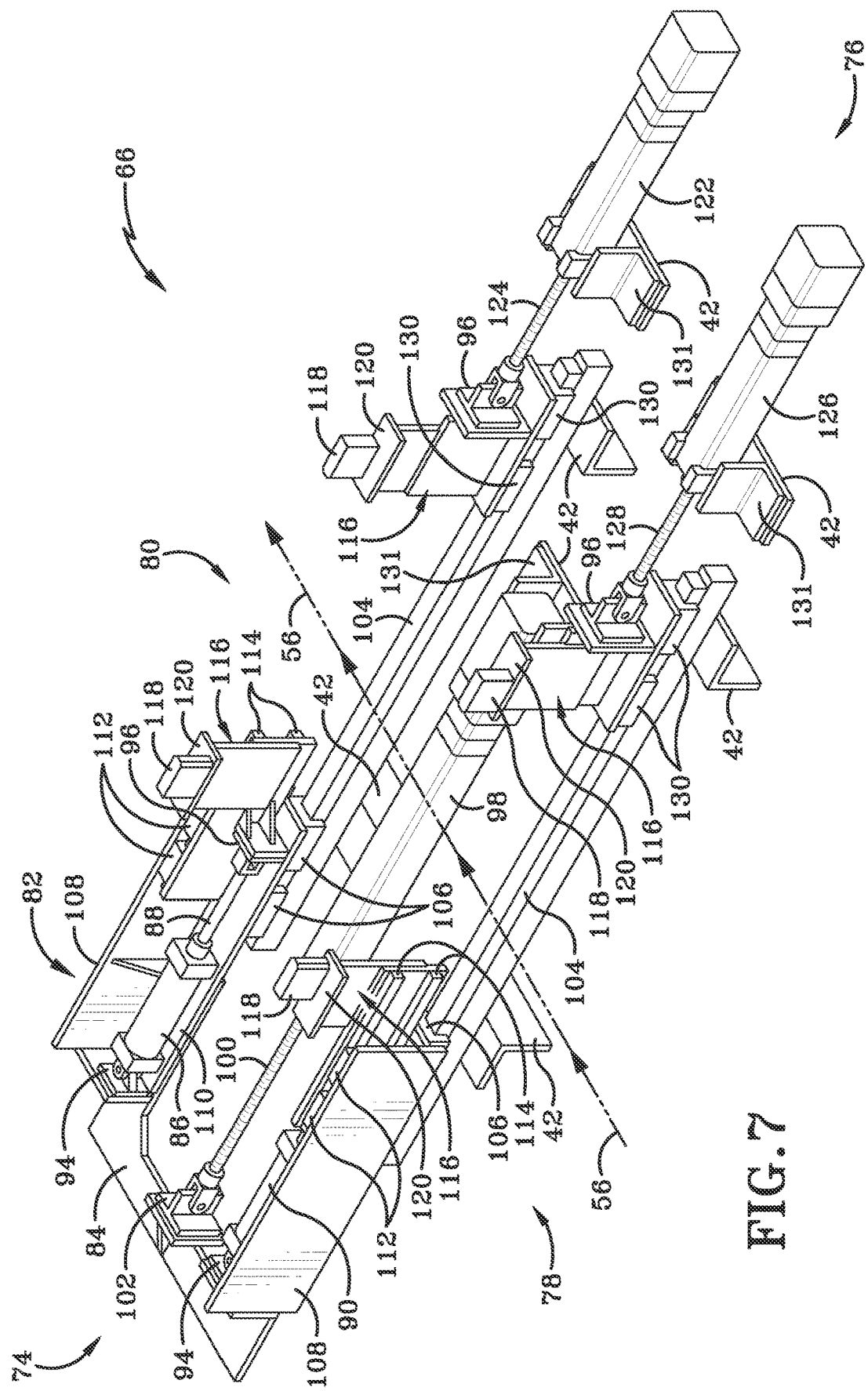
FIG. 7 is a top perspective isometric view of a skewing system of an automated inline rip saw system, according to one aspect of the present disclosure.
Figure 8:
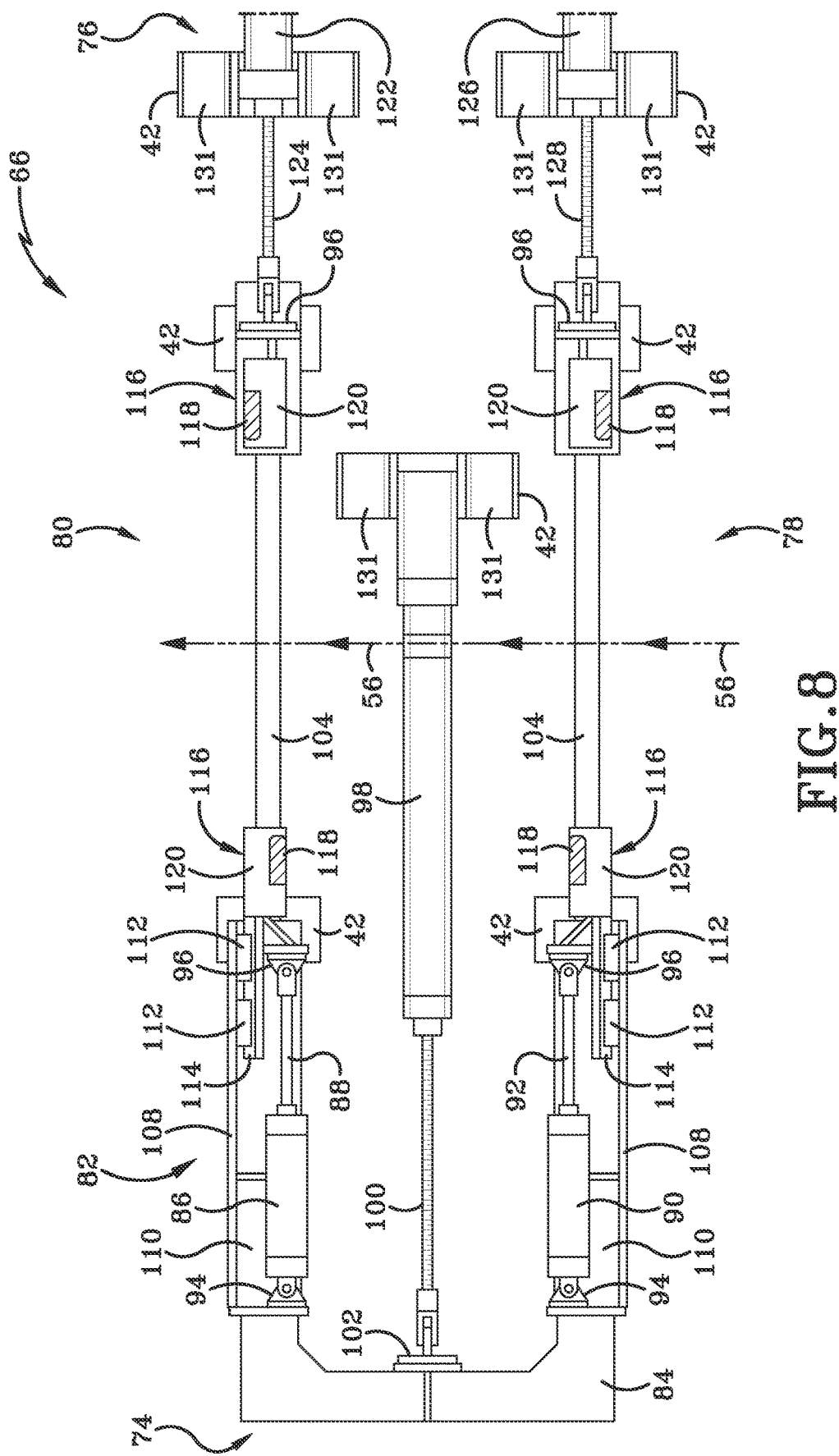
FIG. 8 is a top plan view of the skewing system of FIG. 7.
Figure 9:
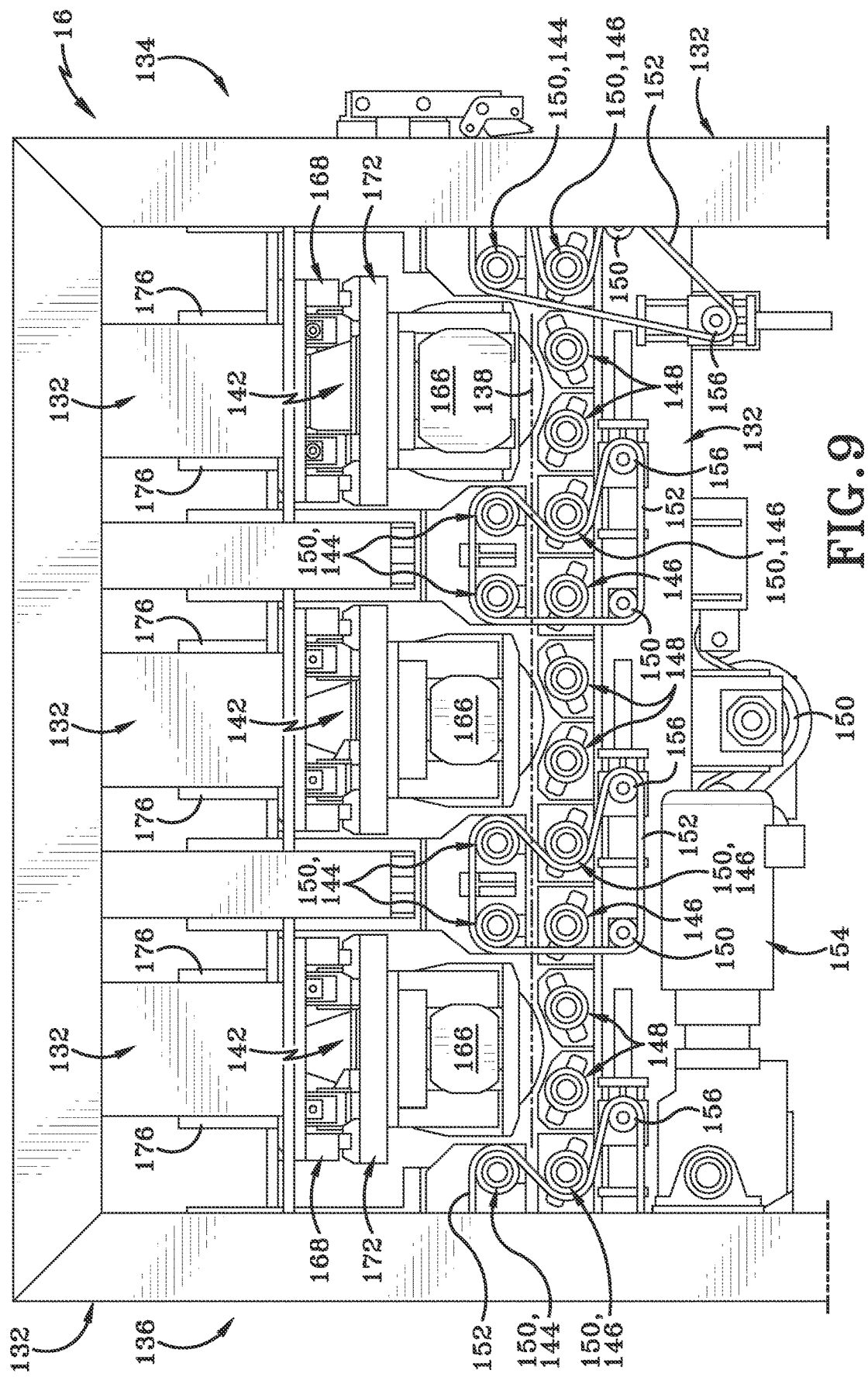
FIG. 9 is a front elevation view of a cutting unit of an automated inline rip saw system, according to one aspect of the present disclosure.

Skewing unit 14 may further include a skewing assembly 66, which may perform the operational skewing of a piece of wood traveling down path 56. Skewing assembly 66, as best seen in FIGS. 6-8, may be positioned towards second end 46 of skewing unit 14 and may further include one or more upper skewing roller assemblies 68, including one or more upper skewing rollers 70 therein. These rollers 70 may be substantially similar or identical to upper rollers 50 but for their placement, operation, and function in the skewing process, as discussed further herein. Further, as best seen in FIG. 5, these upper skewing rollers 70 and roller assemblies 68 may be controlled by actuator and piston assemblies 72, which may allow skewing rollers 70 to move vertically. According to one aspect, skewing assembly 66 may have two upper skewing roller assemblies 68; however, it will be understood that any suitable number of skewing roller assemblies 68 and skewing rollers 70 may be utilized, as dictated by the desired implementation. Similarly, skewing unit 14 and skewing assembly 66 may be scaled up or down in size, as dictated by the desired implementation and use thereof.

With continued reference to FIGS. 3-8, but with particular reference to FIGS. 7 and 8, the skewing assembly 66 will now be described in further detail. Skewing assembly 66 may generally extend transversely across the path 56 wood would take through the skewing unit 14. Skewing assembly 66 may therefore have a first end 74 spaced transversely opposite a second end 76, and a first side 78 spaced longitudinally across from a second side 80. As oriented in skewing unit 14, skewing assembly 66 may be generally positioned such that path 56 through skewing unit 14 passes from first side 78 to second side 80, as best seen in FIG. 7 and discussed further herein.

Skewing assembly 66 may have two main sections, with a first section at first end 74 being adjustable relative to frame 42. This first section is indicated at reference 82 and may include a sled 84 carrying a first skewing actuator 86 and first skewing piston 88 and a second skewing actuator 90 and second skewing piston 92. First and second skewing actuators 86 and 90 may be secured to sled 84 via actuator mounts 94 while first and second skewing pistons 88 and 92 may be secured thereto through piston mounts 96. As discussed further below, these actuators 86, 90 and pistons 88, 92 may allow skewing assembly 66 to skew a board (such as board 202) or piece of wood moving down path 56, as discussed further below.

Sled 84 may be adjustable, utilizing a centrally mounted coarse adjustment actuator 98 and coarse adjustment piston 100. Coarse adjustment actuator 98 may be supported to frame 42 of skewing unit 14 by brackets 131 at one end, while piston 100 may be connected to sled 84 via piston mount 102 on an opposite end. Each of first skewing actuator 86, first piston 88, second skewing actuator 90, second piston 92, coarse adjustment actuator 98, and coarse adjustment piston 100 (collectively referred to as actuator assemblies, which may further include third and fourth skewing actuators and pistons 122-128, discussed below) may be any suitable actuator and piston assembly, including pneumatic, hydraulic, worm gear, or screw type actuators and piston assemblies, or any suitable combination thereof. These actuator assemblies may be automatically controlled by a computer or processor in communication with other components of rip saw system 10 including scanning unit 12, skewing unit 14, and/or cutting unit 16. For example, actuator assemblies may be controlled by a processor based on the scan data collected and processed by first and second scanners 20 and 22, as discussed herein.

Sled 84 may be mounted on rails 104 via sliders 106, which may allow slidable engagement therewith. Sliders 106 may further include an anti-friction coating or insert (not shown) which may reduce friction between sliders 106 and rails 104. According to one aspect, sliders 106 may be polished or coated to reduce friction, or alternatively may include a separate insert formed of any suitable material such as polished or coated metal, plastic, high density polyethylene or other polymers, or the like, or suitable combinations thereon. Sled 84 may further include side plates 108 and base plates 110, which may form the body and/or mounting surfaces for actuator mounts 94 and coarse adjustment piston mount 102.

Sled 84 may further support skewing arms 116, which may include sliders 112 and side rails 114, as well as skewing pins 118 and support plates 120. Sliders 112 and rails 114 may be substantially similar to rails 104 and sliders 106, but for their placement and orientation in skewing arms 116. In particular, skewing arms 116 may be slidably engaged with sled 84 to allow skewing arms 116 to move independently of sled 84 for fine adjustments, as discussed further in regards to the operation of skewing assembly 66 below. Skewing pins 118 may be operationally connected to and supported support plates 120, and may be the portion of skewing arms 116 which may interact with a piece of wood to be skewed, as discussed further herein.

Opposite first section 82 is second side 76 of skewing assembly 66 which may include a third skewing actuator 122, a third skewing piston 124, a fourth skewing actuator 126, and a fourth skewing piston 128. As with first and second skewing actuators 86, 90 and pistons 88, 92, third and fourth skewing actuators 122, 126 and pistons 124, 128 may be any suitable actuator and piston assemblies, including pneumatic, hydraulic, worm gear, screw type or the like. As mentioned above, references to actuator assemblies generally will be understood to include third and fourth skewing actuators 122, 126 and pistons 124, 128 unless specifically stated otherwise.

As with first and second skewing actuators 86, 90 and pistons 88, 92, third and fourth skewing actuators 122, 126 and pistons 124, 128 may further provide for fine adjustment of a board 202 as it moves through skewing unit 14, as discussed further below. Third skewing actuator 122 and fourth skewing actuator 126 may be fixedly attached to frame 42 via mounting brackets 131 while third and fourth skewing pistons 124 and 128 may be operationally connected to additional skewing arms 116 via piston mounts 96. These skewing arms 116 may be substantially identical to skewing arms 116 of first and second skewing actuators 86, 90 and pistons 88, 92 except that the skewing arms 116 of third and fourth skewing actuator assemblies may include sliders 130, which may be substantially similar or identical to sliders 106 in that they may slidably interact with rails 104 to allow the longitudinal movement thereof.

Further discussion of skewing unit may be best provided through the discussion of the operation and use thereof. Accordingly, skewing assembly 66 may be further described below with regards to the operation of rip saw system 10.

With reference to FIGS. 9-15, cutting unit 16 will now be described. Cutting unit 16 may have a frame 132 which may generally be a support frame and may include any suitable connections, mounts, brackets, supports, or the like to carry or otherwise connect to the various components of cutting unit 16 and will be understood to further include any necessary mounting surfaces, hardware, and the like, as well as all necessary or desired components for the proper operation thereof. For example, frame 132 may support each element of cutting unit 16 and may further support electrical wiring, electrical systems, and the like, as desired.

Cutting unit 16 may have a first end 134 defined as the end oriented towards or adjacent to skewing unit 14 and a second end 136 opposite therefrom. Cutting unit 16 may further define a path 138 from first end 134 to second end 136 thereof (which, along with paths 30 and 56, may further complete the path 200 through system 10, as discussed below).

Cutting unit 16 may further include a housing 140 fully or partially enclosing the components of cutting unit therein. Housing 140 (best seen in FIG. 1 but removed in whole or in part in FIGS. 9-15 for clarity). Housing 48 may be constructed of any suitable material and may include one or more removable panels, viewing windows, access doors, or the like to allow an operator access to the components contained therein for maintenance, repair, or other similar activities. Housing 40 may further include any and all mounting hardware, fasteners, or the like as well as any necessary additional components including wiring switches or other similar such elements, as dictated by the desired implementation.

Cutting unit 16 may include one or more saw assemblies 142 which may be operable to cut a piece of wood moving on path 138 through cutting unit 16, as discussed further below. As shown and described herein, cutting unit 16 may have as many as three saw assemblies 142 having a total of six saw blades 162; however, cutting unit 16 may be scaled up or down to include any number of suitable saw blades 162 and saw assemblies 142 as desired or dictated by the desired implementation thereof. For purposes of clarity in the disclosure as discussed further herein, saw assemblies 142 may be substantially identical unless specifically stated otherwise; however, it will be further understood that saw assemblies 142 may vary within a single cutting unit 16, as discussed below.

Cutting unit 16 may further include a plurality of upper rollers 144 and lower rollers 146 which may be substantially similar to upper and lower rollers 26, 28, 50, and 52 but for their placement and function within rip saw system 10. Both upper and lower rollers 144 and 146 (and saw rollers 148, discussed below) may be formed of any suitable material, including steel or other metals, polymers, plastics, or the like and may include a surface texture to aid in gripping or otherwise moving wood down path 138 in cutting unit 16. Rollers 144, 146, and 148 may be mounted in a sufficient manner as to permit them to rotate about a longitudinal axis running through each individual roller 144, 146, and 148. Rollers 144, 146, and 148 may further include a projection, extension, flange, groove, channel, or similar feature to permit interaction between rollers 144, 146, and 148 and any drive components including any drive belts 152 or the like associated therewith and/or with any drive motor 154, as discussed further below.

Upper rollers 144 may be powered or unpowered, and may be arranged in sets, as discussed above with respect to rollers 26 and 50. Further, upper rollers 144 may include one or more actuator and piston assemblies which may be identical to actuator and piston assemblies 54, and are therefore referenced at 54 in cutting unit as well. These actuator and piston assemblies 54 may allow vertical movement of upper rollers 144 as desired.

Lower rollers 146 may correspond to upper rollers 144 and may be considered powered rollers in that they may include one or more drive rollers 150 and one or more drive belts 152, which may be operable to connect rollers 146 to a drive motor 154. Drive motor 154 may be any suitable motor, including but not limited to servo motors or the like. Drive motor 154 may operable to power drive rollers 150 and belts 152 which in turn may further drive lower rollers 146.

Upper and lower rollers 144, 146 may be operationally connected in that they may all be driven via the same motor 154 and may therefore rotate in unison. Alternatively, one or more upper and/or lower rollers 144, 146 may have separate dedicated motors 154 to allow multiple modes of operation, as dictated by the desired implementation thereof.

Saw unit 16 may further include one or more sets of saw rollers 148, which may be substantially identical to lower rollers 146 but may be oriented or positioned in a way to provide clearance for saw blades 162, as discussed further below. According to one example, saw rollers 148 may have a groove or indentation therein to allow clearance for a saw blade 162. According to another aspect, saw rollers 148 may be shorter in transverse length to allow clearance for saw blades 162.

Figure 10:
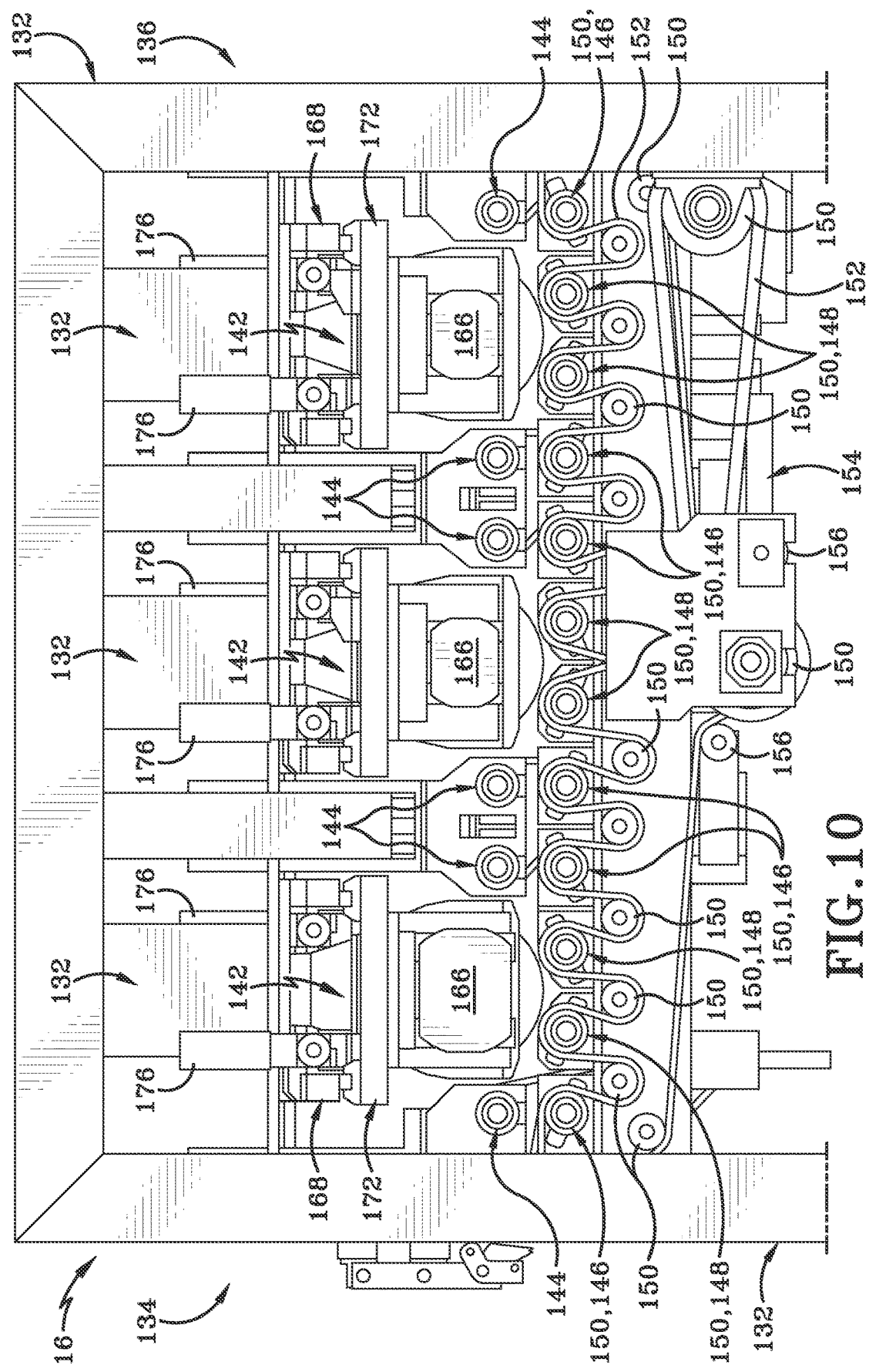
FIG. 10 is a rear elevation view of the cutting unit of the automated inline rip saw system, according to one aspect of the present disclosure.
Figure 11:
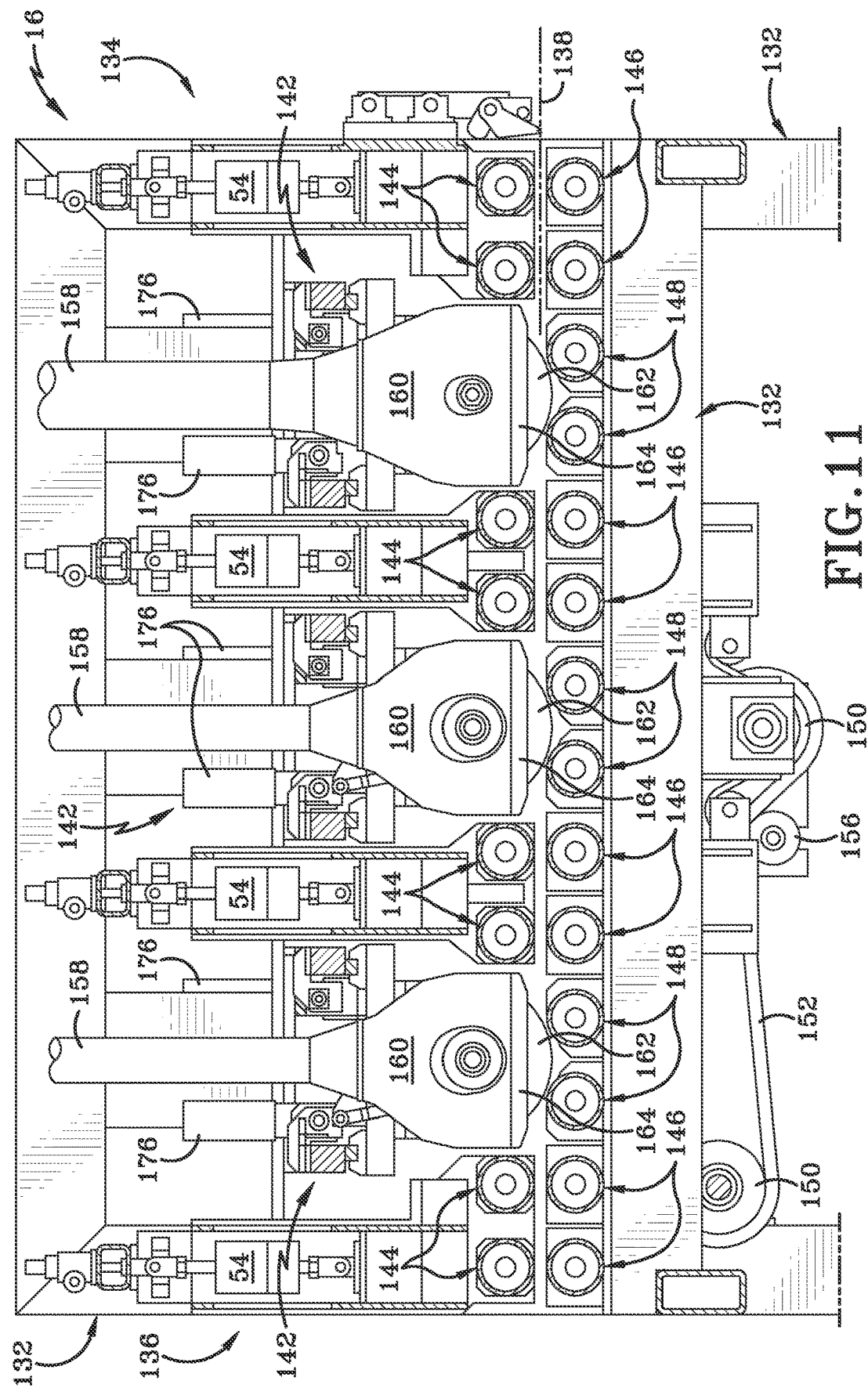
FIG. 11 is a front elevation cross section view of the cutting unit, according to one aspect of the present disclosure.
Figure 12:
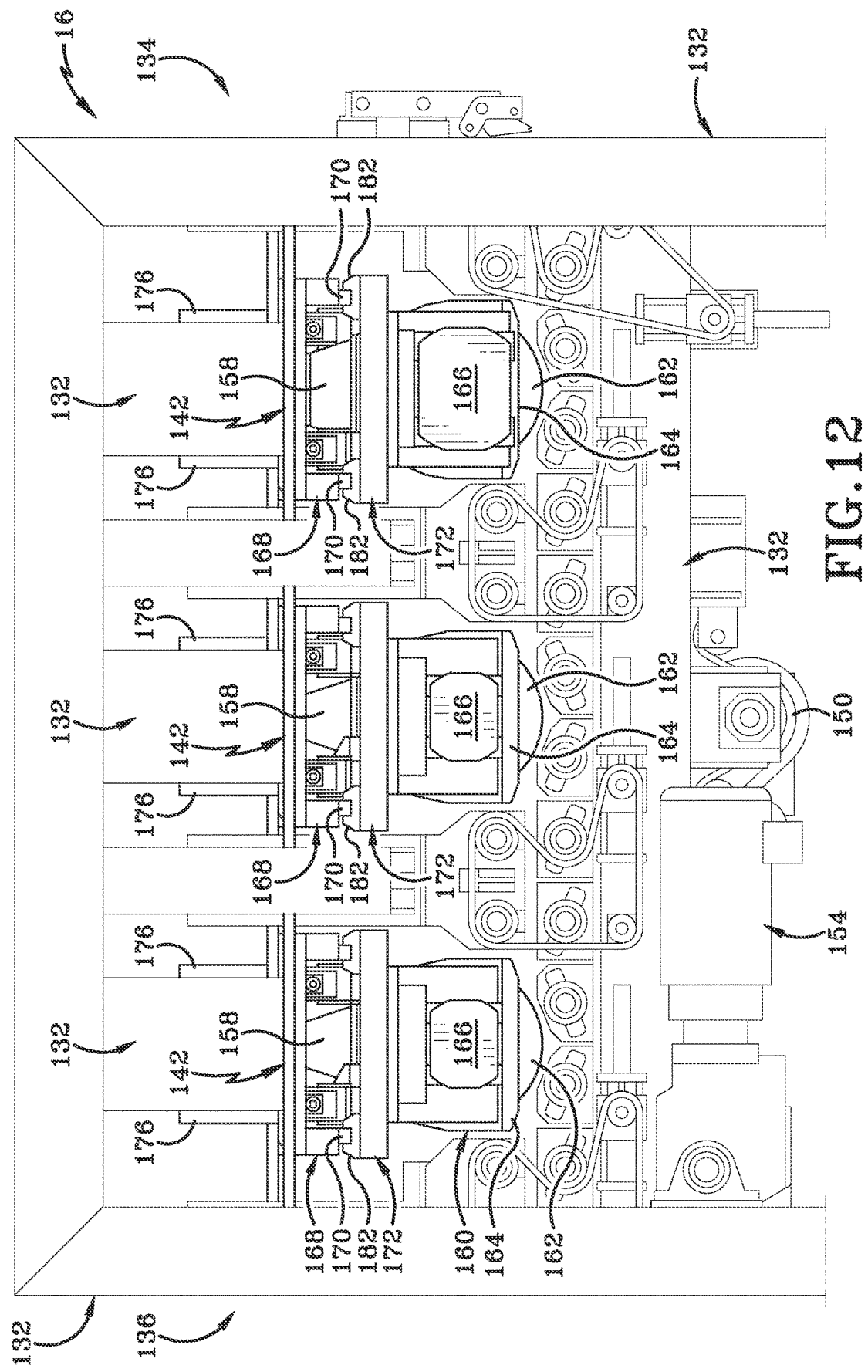
FIG. 12 is a front elevation view of the cutting unit of FIG. 10 with the saw assemblies distinguished of the automated inline rip saw system, according to one aspect of the present disclosure.

With continued reference to FIGS. 9-15, but particular reference to FIG. 10, one or more of drive belts 152 may be a serpentine belt which may connect to all or substantially all upper, lower, and saw rollers 144, 146, and 148, or any suitable or desired combination thereof. Collectively, whether driven in unison, in separate sets, or individually, it will be understood that upper rollers 144, lower rollers 146, and saw rollers 148 may be generally operable to move wood down path 138 and through cutting unit 16, similar to the manner in which wood is moved through scanning unit 12 and skewing unit 14.

Cutting unit 16 may further include a dust removal system having a vacuum or the like including dust removal conduits 158, which may be in operable communication with saw assemblies 142, as discussed further herein. This dust removal system may be an industry standard dust removal vacuum, HVAC system, or the like, and may operate according to known and expected principles to manage or otherwise control dust buildup within cutting unit 16. Similarly, as discussed below, wherein hogging saw blades may be employed, cutting unit 16 may further include a collection assembly and/or device to collect wood chips or particles hogged from a piece of wood as it moves through cutting unit 16, as dictated by the desired implementation and discussed further herein.

With continued reference to FIGS. 9-15, but particular reference to FIGS. 11-15, saw assemblies 142 will now be described in further detail. As mentioned above, multiple illustrated saw assemblies 142 may be substantially identical unless specifically stated otherwise. Accordingly, it will be understood that discussion of saw assemblies 142 and their various components is equally applicable to any suitable number of saw assemblies 142 included or otherwise present within cutting unit 16.

Saw assembly 142 may include a dust hood 160, which may partially enclose a saw blade 162 therein. Dust hood 160 may be in operable communication with the dust removal conduits 158 via a coupling sleeve 198 to allow the vacuum system to be applied above each saw blade 162 for dust collection therefrom. Each dust hood 160 may further include a foot portion or foot 164. Dust hood 160 and foot 164 are discussed in more detail below.

Figure 13:
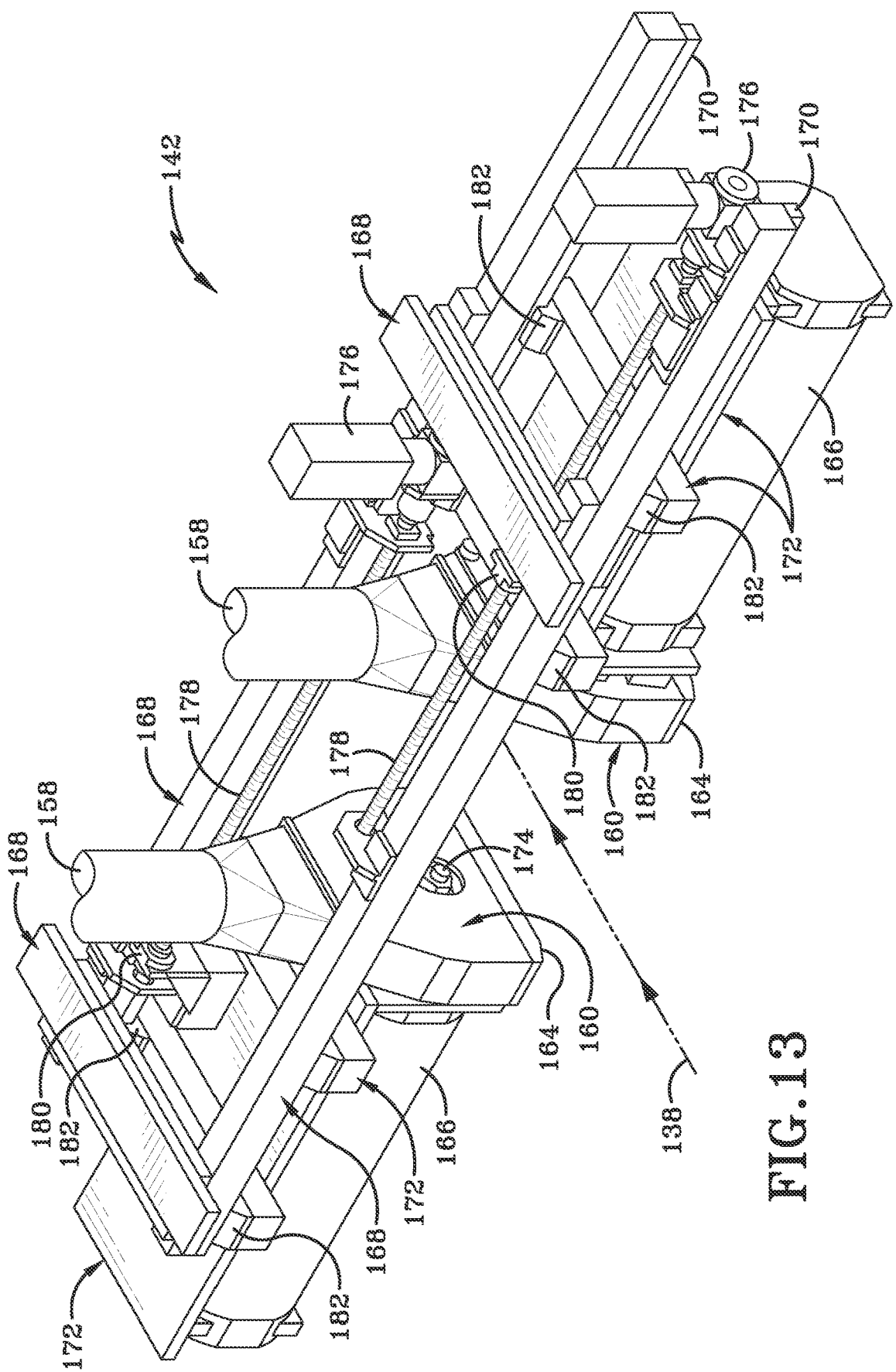
FIG. 13 is a top perspective isometric view of an exemplary saw assembly of the automated inline rip saw system, according to one aspect of the present disclosure.
Figure 14:
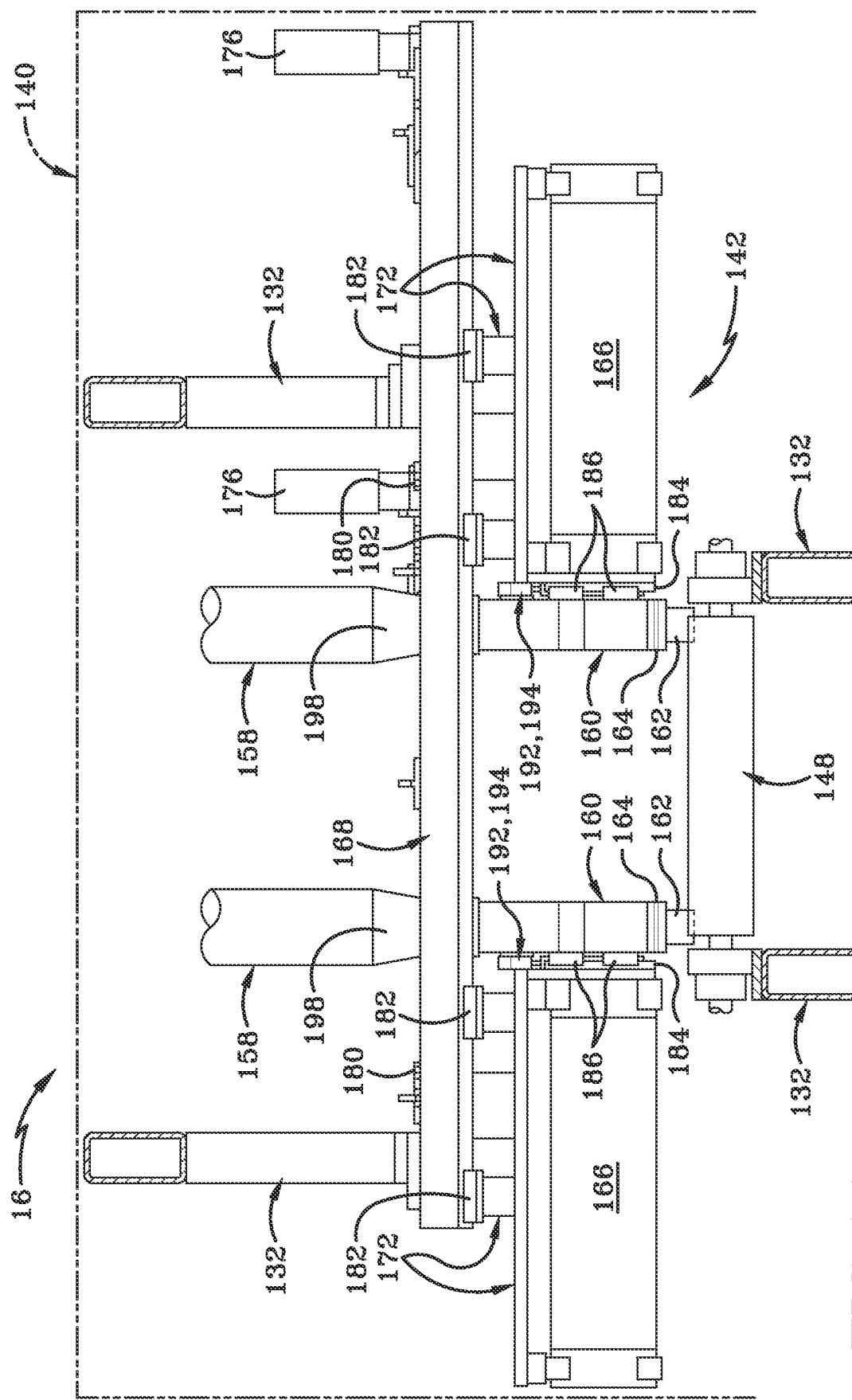
FIG. 14 is a side elevation partial cross section view of the cutting unit showing the saw assembly installed therein, according to one aspect of the present disclosure.

With continued reference to FIGS. 9-15, but particular reference to FIGS. 13 and 14, saw assemblies 142 may be provided such that each saw blade 162 is operably connected to a separate dedicated motor 166 such that there is one saw blade 162 per motor 166. As shown and described herein, motor 166 may be a dedicated arbor motor, or may be any other suitable motor type operable to power saw blades 162. Accordingly, where cutting unit 16 includes three saw assemblies 142 (as shown), each saw assembly 142 is contemplated to have two blades 162 with two arbor motors 166, providing six total blades 162 and six total arbor motors 166 in the illustrated and discussed example. Further, as each blade 162 has its own dedicated dust hood 160 in the exemplary configuration shown and described herein, saw assemblies 142 would likewise include a total of six dust hoods 160.

Saw assemblies 142, an example of which is shown isolated in FIG. 13 for clarity, may be mounted on a saw assembly frame 168, which may generally be a support frame and may include any suitable connections, mounts, brackets, supports, or the like to carry or otherwise connect to the various components of saw assemblies 142 and will be understood to further include any necessary mounting surfaces, hardware, and the like, as well as all necessary or desired components for the proper operation thereof. For example, saw assembly frame 168 may support each element of saw assemblies 142 and may further support electrical wiring, electrical systems, and the like, as desired.

Saw assembly frame 168 may further include a pair of rails 170 which may extend transversely to path 138 through cutting unit 16 to allow saw blades 162 to be positioned for longitudinal rip cuts on a piece of wood moving through cutting unit 16, as discussed further below with regards to the operation of rip saw assembly 10. Each individual saw assembly 142, having two blades 162 and two arbor motors 166, may likewise have two mounting sleds 172 which may slidably engage rails 170 via sliders 182. Sliders 182 may include an anti-friction coating or insert (not shown) which may reduce friction between sliders 182 and rails 170. According to one aspect, sliders 182 may be polished or coated to reduce friction, or alternatively may include a separate insert formed of any suitable material such as polished or coated metal, plastic, high density polyethylene or other polymers, or the like, or suitable combinations thereon.

Figure 15:
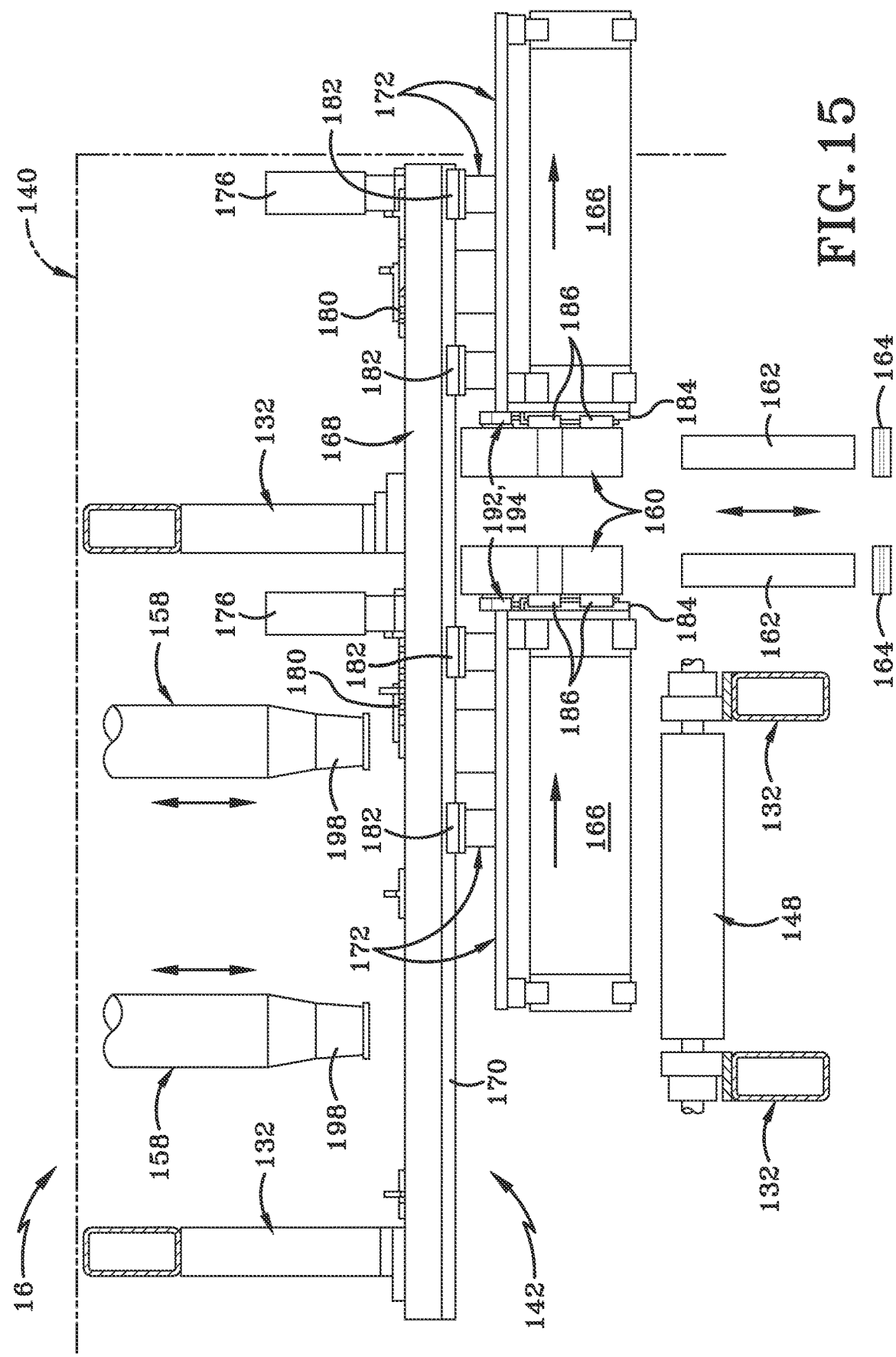
FIG. 15 is a side elevation operational view of a saw assembly of an automated inline rip saw system, according to one aspect of the present disclosure.

Sleds 172 may each support one arbor motor 166, saw blade 162, and dust hood 160, and the related components thereon. As discussed further below and as best seen in FIG. 15, the slidable engagement of mounting sleds 172 with rails 170 via sliders 182 may allow each saw blade 162 and arbor motor 166 to move transversely relative to path 138 to position saw blades relative to a piece of wood to remove defects therefrom, but also to provide easy and quick access for changing out saw blades 162 or other maintenance activities, as necessary.

Saw blades 162 may be any suitable style blade and may include one or more hogging blades for rough removal of large sections of a piece of wood or any other suitable rip saw blade, including fine edging blades or the like. Saw blades 162 may be commercially available blades and may be scaled to any suitable size, as dictated by the desired implementation and may similarly include any suitable or desired features thereof.

Saw assemblies 142 may further include longitudinal adjustment mechanism 176, which may be a mechanical screw having a shaft 178 and threaded receivers 180. This adjustment mechanism 176 may be operable to move sleds 172, arbor motors 166, dust hoods 160, and saw blades 162 longitudinally along rails 170, as described further herein. According to another aspect, adjustment mechanism 176 may be any suitable adjustment type mechanism operable to move mounting sleds 172 longitudinally along rails 170.

With continued reference to FIGS. 9-15, but particular reference to FIGS. 14 and 15, saw assembly 142 may further include one or more vertical rails 184, which may engage with vertical sliders 186 to allow vertical movement of dust hoods 160, as discussed further below. Vertical rails 184 and sliders 186 may be substantially similar to slides 182 and rails 170 in that they may interact and operate in a substantially similar way, but may otherwise vary in size, placement, and purpose within saw assemblies 142. Saw assemblies 142 may likewise include one or more stop members (not shown) that may define the limit to which sliders 182 and/or vertical sliders 186 may travel.

With reference to FIG. 15 and as discussed further herein, saw assembly 142 may be slidable to a position wherein saw blades 162 and hoods 160 may be accessed through access panels in housing 140 of cutting unit 16. This may allow for ease of maintenance and replacement of saw blades and other parts, as desired.

Figure 16:
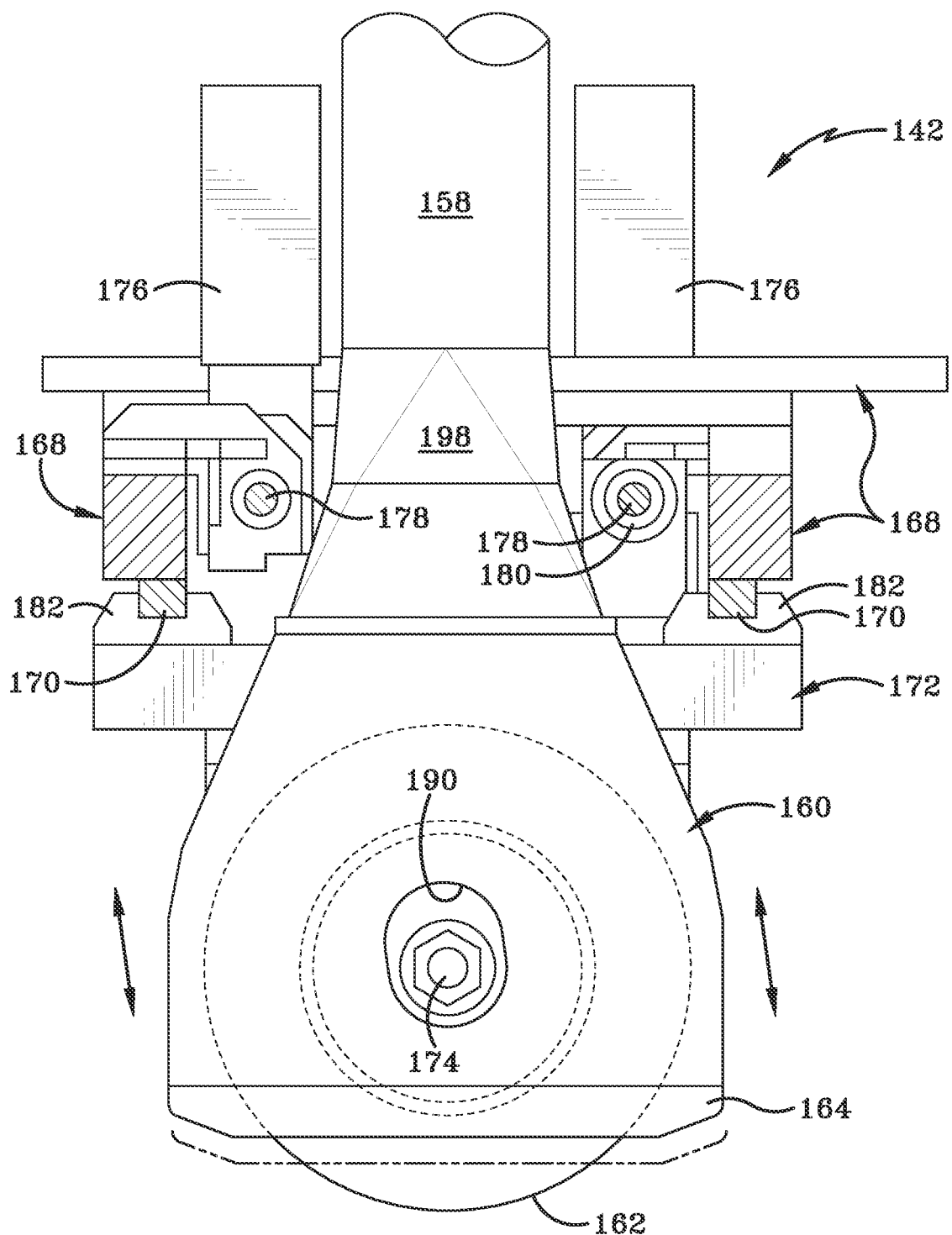
FIG. 16 is a side elevation operational view of a saw assembly, according to one aspect of the present disclosure.
Figure 17:
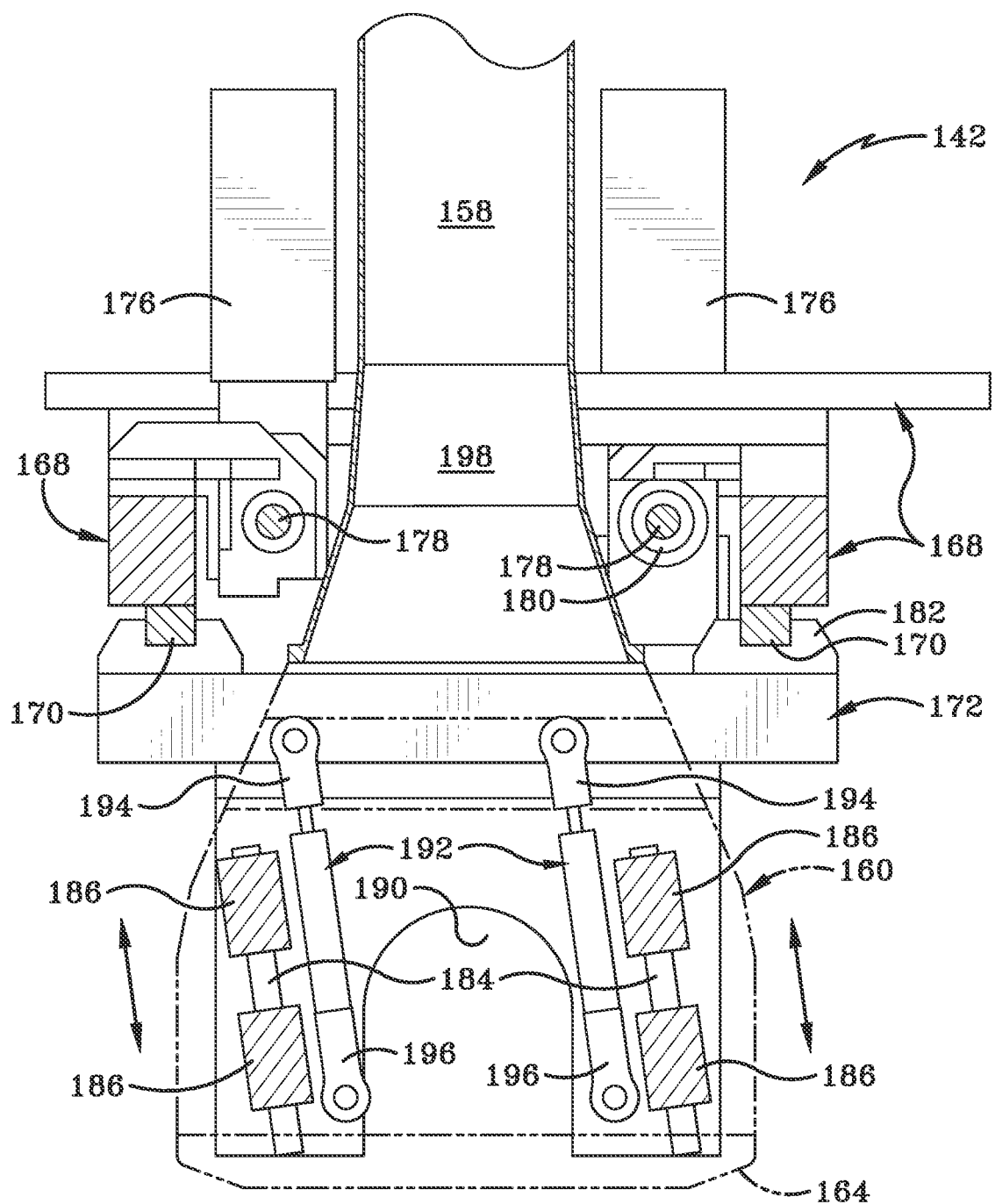
FIG. 17 is a side elevation cross section view of a saw assembly of the automated inline rip saw system, according to one aspect of the present disclosure.
Figure 18:
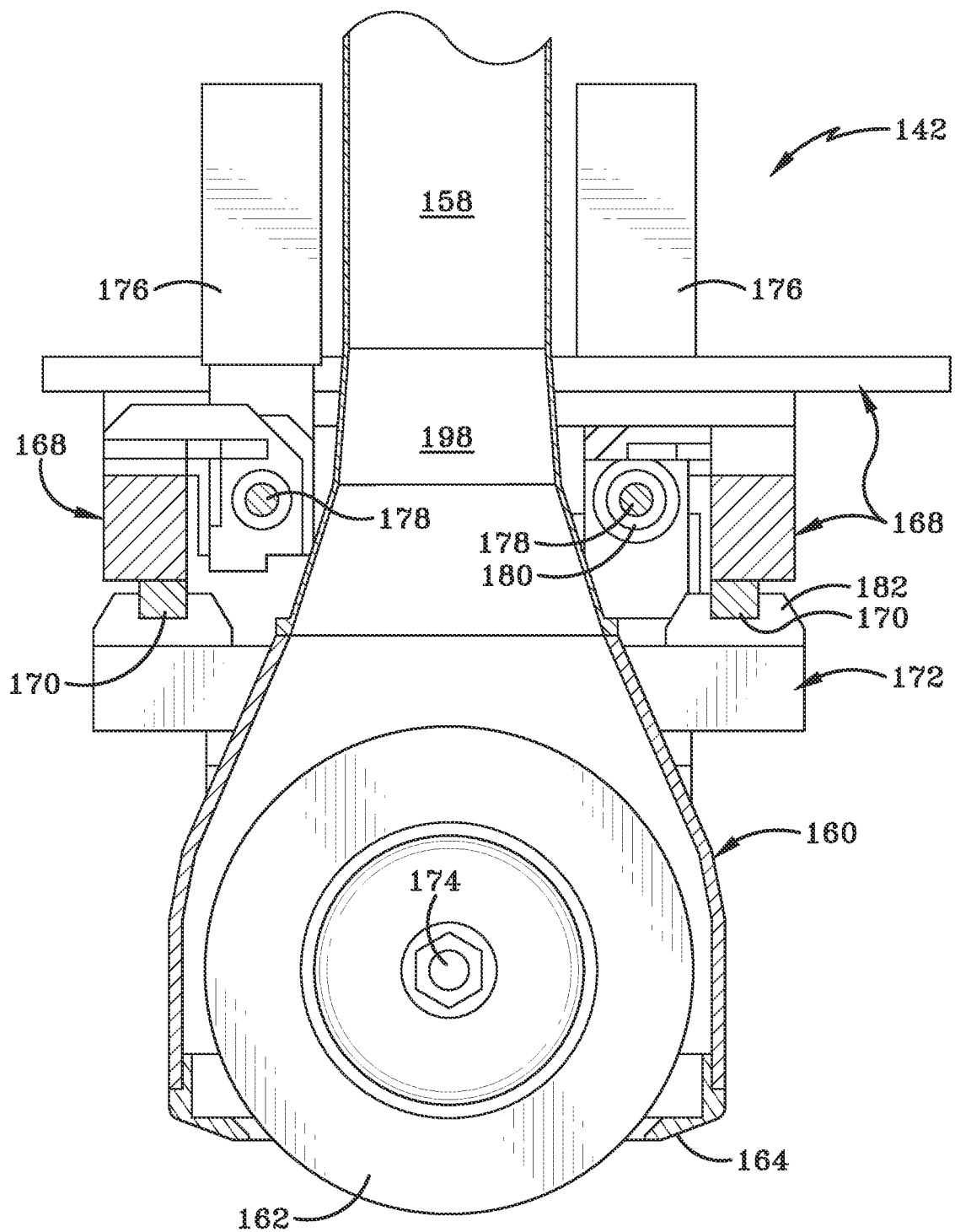
FIG. 18 is a side elevation cross section view of a second saw assembly of the automated inline rip saw system, according to one aspect of the present disclosure.

With reference to FIGS. 16-18, dust hood 160 may be any suitable dust hood operable to enclose or partially enclose saw blades 162 therein while simultaneously removing saw dust particles from cutting unit 16 via a vacuum system, as mentioned above. Dust hood may be constructed of any suitable material and may be scaled in size to accommodate saw blades 162 of varying size and/or function therein. Dust hoods 160 may be removable attached to conduits 158 through coupling sleeve 198 or other similar mechanism which may allow dust hood 160 to be disconnected from conduit 158 when saw assemblies 142 are moved for maintenance. Similarly, dust hood 160, coupling sleeve 198, and conduit 158 may be flexible in that they may bend, flex, or otherwise move with saw assemblies 142 during the operation thereof, discussed below.

Dust hoods 160 may further interact with saw blades 162 and sleds 172 in a vertically adjustable manner. In particular, dust hoods 160 may adjust vertically relative to saw blades 162 and arbor motors 166. To accommodate such vertical movement, dust hoods 160, may further include an elongated slot or opening 190 to allow clearance for the saw blade 162 when dust hood 160 moves. Further, dust hood 160 may include one or more actuator and piston assemblies 192, which may be attached to the mounting sled 172 via a piston mount 194 and attached to the dust hood 160 via an actuator mount 196 to effectuate the vertical movement thereof. Actuator and piston assemblies 192 may be any suitable actuator and piston assemblies, including pneumatic, hydraulic, or the like. These actuator and piston assemblies 192 may operably cause the vertical movement of the dust hood 160, as discussed with reference to the operation of rip saw system 10 below.

Foot 164 may be constructed of any suitable material and may generally be the portion of the dust hood 160 that is closest to and interacts with a piece of wood within cutting unit 16. Foot 164 may extend around saw blade 162 and may form at least a partial seal between the dust hood 160 and the piece of wood and around saw blade 162 for efficient dust removal during the cutting process. Foot 164 may be further operable to secure the piece of wood within cutting unit 16 during the cutting process.

Having generally discussed the elements and components of rip saw assembly 10, the method and manner of use therefore will now be described. For purposes of this operational section, path 30 through scanning unit 12, path 56 through skewing unit 14, and path 138 through cutting unit 16 will be collectively referred to as path 200, which will be understood to be a reference to the entire path a piece of wood 202 may take through rip saw system 10. Where references to path 200 is intended to refer to only a portion of the path and not the entire path 200, the specific reference numbers for the portion of the path will still be utilized (i.e. paths 30, 56, and/or 138).

The operation and methods of use for rip saw system 10 will be described with general reference to FIGS. 19-24. Accordingly, solely for purposes of clarity in the discussion of the operation, several reference numbers have been omitted from these figures.

Figure 19:
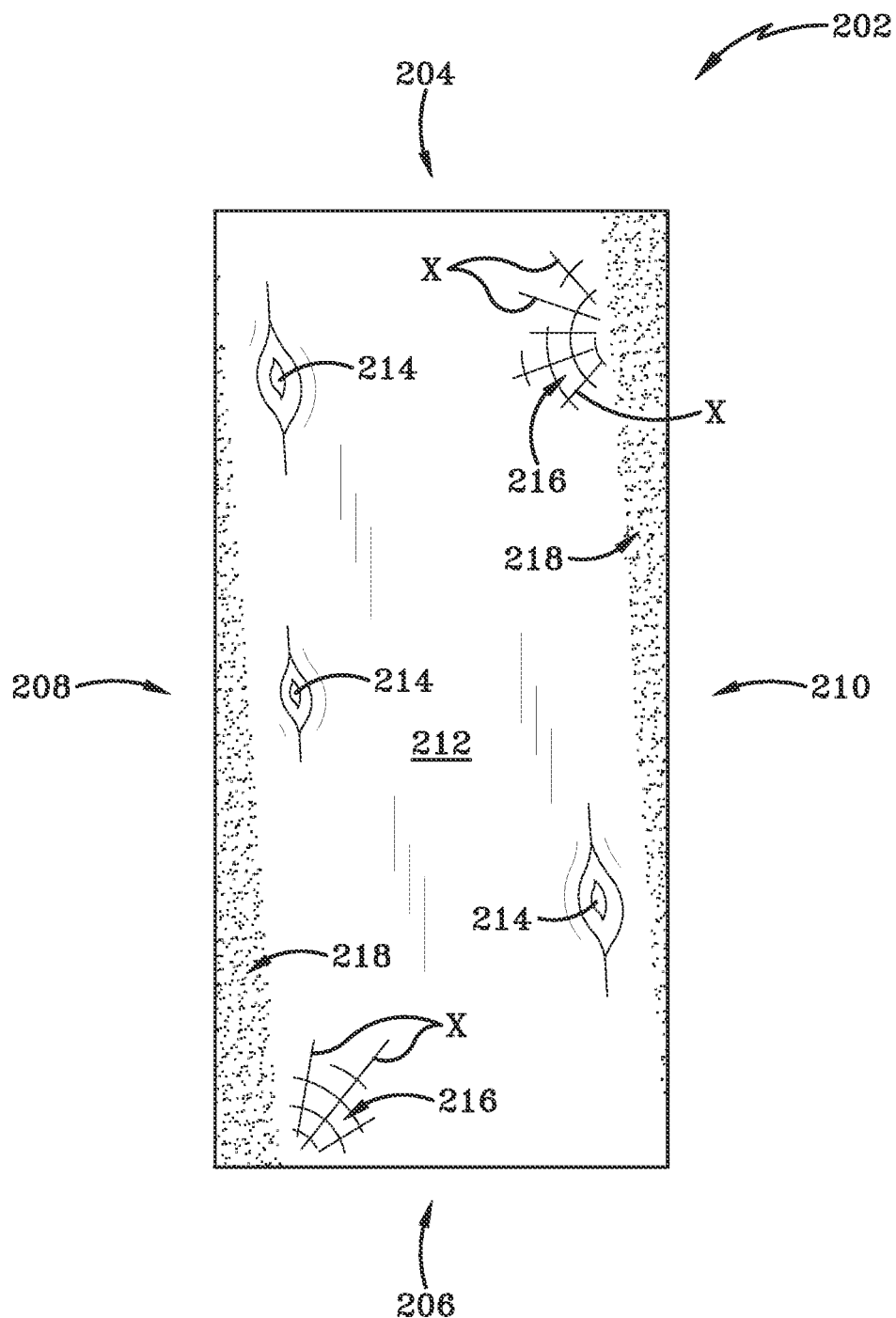
FIG. 19 is an overhead plan view of an exemplary board prior to scanning and cutting, according to one aspect of the present disclosure.

With reference to FIG. 19, an exemplary piece of wood 202 is shown and will be generally referred to as board 202; however, it will be understood that board 202 is an example and could be interchanged with any suitable piece of wood having any suitable size, shape, or orientation. Accordingly, board 202 may have a first end 204 spaced apart from a second end 206 and defining a longitudinal direction therebetween. The distance between first and second ends 204 and 206 may generally define the length of board 202. First end 204 and second end 206 may be oriented such that first end 204 may be the end of board 202 that is first inserted into path 200 for processing. Thus, the longitudinal direction is contemplated to be parallel to the path 200 through rip saw system 10 at the point of insertion into path 200. Board 202 may further have a first side 208 spaced apart from a second side 210 and defining a lateral or transverse direction therebetween, with the distance therebetween further defining the width of board 202. Board 202 may have a top surface 212 (defined as the surface facing upwards when board 202 is in rip saw system 10) and a bottom surface (not shown) vertically opposite therefrom and defining the thickness of board 202.

Board 202 may further include one or more flaws or features to be scanned and accounted for and/or removed from board 202. These flaws or features are shown as knots 214, rays 216, and sapwood 218. These knots 214, rays 216, and sapwood 218 are shown as examples and may or may not be present in each board 202 being processed by rip saw system 10. Similarly, these features may not be identical within a single board 202 or across multiple boards 202. Accordingly, it will be understood that these features are merely representative of some of the types of features that may be detected and/or removed by rip saw system 10 and are not limiting examples thereof.

Knots 214 are generally compressed areas formed in wood that are greater in density than the surrounding wood. Accordingly, knots 214 can be less desirable in high quality wood as the transition and variation in density can lead to cracks, breakage, or in the use as a barrel stave, permeability of liquid. In particular, the boundaries of a knot 214 where it meets the heartwood are prone to separation and leakage when utilized in applications where water permeability is not desired. Knots 214 are relatively easy to locate and identify as compared to rays 216 and sapwood 218.

Rays 216 are features found in wood formed from vascular tissue in the tree and can likewise be liquid permeable, particularly when an individual ray 216 runs at an angle 45° or greater to the direction of the grain of the wood. Examples of potentially problematic rays 216 on board 202 are indicated at the references marked with an X. Rays 216 are relatively difficult to detect with any reliable scans as the depth of rays 216 in any particular piece of wood cannot be determined by an optical surface scan and the rays themselves do not show up or are not differentiated from surrounding wood in x-ray scans.

As mentioned above, detecting rays 216 within a board 202 is difficult. While optical surface scans can detect exposed rays 216 visually, there is no indication of the depth of visible rays 216 in the board. Further, optical surface scans cannot detect rays 216 that are present inside a board 202 but do not reach the surface thereof. Again, rays 216 likewise do not show up in x-rays; however, the grain pattern of the wood can be detected by both surface scanning and x-rays, allowing for the detection of rays 216 based on the patterns and variations in the grain of the wood. In particular, certain grain patterns and variations are recognized and indicative of rays 216, and these patterns and variations in the grain can be visualized, analyzed, and used to predict where rays 216 would be found, but may also be used to determine an approximate angle of these rays 216 relative to the direction of the grain. Again, rays 216 running 45° or greater relative thereto are not desirable. Using the combination of x-ray scanning and optical surface scanning to visualize the grain of the wood allows these problematic rays 216 to be located and removed from the board 202.

Sapwood 218 is an area of wood that is less dense than the surrounding wood, and tends to be located towards the outer portions of a piece of wood as sapwood typically indicates areas of growth for a tree. Sapwood 218 has a high moisture content and is therefore more permeable to liquids and is less durable than adjacent heartwood. Reliably detecting sapwood 218 in dry wood is difficult as surface scans rarely can differentiate the sapwood 218 from the more desirable heartwood. Detection via x-ray is somewhat more successful than surface scanning because the density variation provides a different x-ray image; however, the differences are subtle and can vary depending on the age and moisture content of the wood. In particular, the older and drier the wood stock, the more difficult it becomes to differentiate sapwood 218 from heartwood with x-ray scanners. Accordingly, as discussed in further detail below, the earlier in the process the wood can be scanned, the more reliable and precise the detection of sapwood 218 can be. According to one aspect, scanning green wood shortly after it is sawn into slats or boards 202 may provide the most accurate detection and removal of sapwood 218, as discussed below.

Accordingly, these features, namely knots 214, rays 216, and sapwood 218 are less desirable for certain wood making applications, including the use of wood in making barrel staves, and it is desirable to accurately and precisely identify and remove these from a board 202 prior to its end use. In doing so, the combination of using both x-ray scanning in first scanner 20 and optical scanning in second scanner 22 allows for a more precise detection, identification, and removal of these flaws. In turn, less waste is produced and the yield is higher as a result.

Figure 19A:
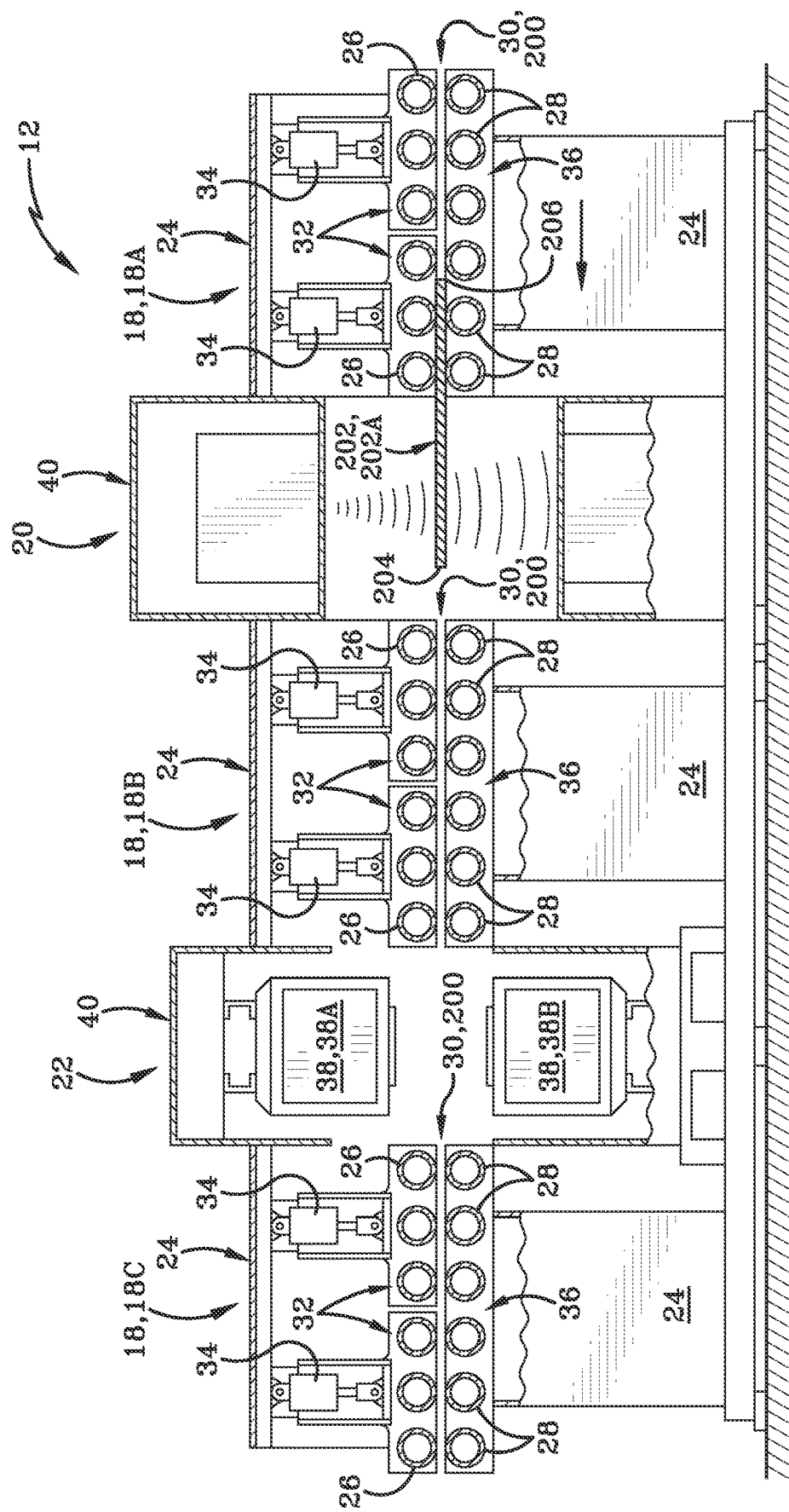
FIG. 19A is a front elevation partial cross section operational view of a scanning unit of the automated inline rip saw system, according to one aspect of the present disclosure.
Figure 19B:
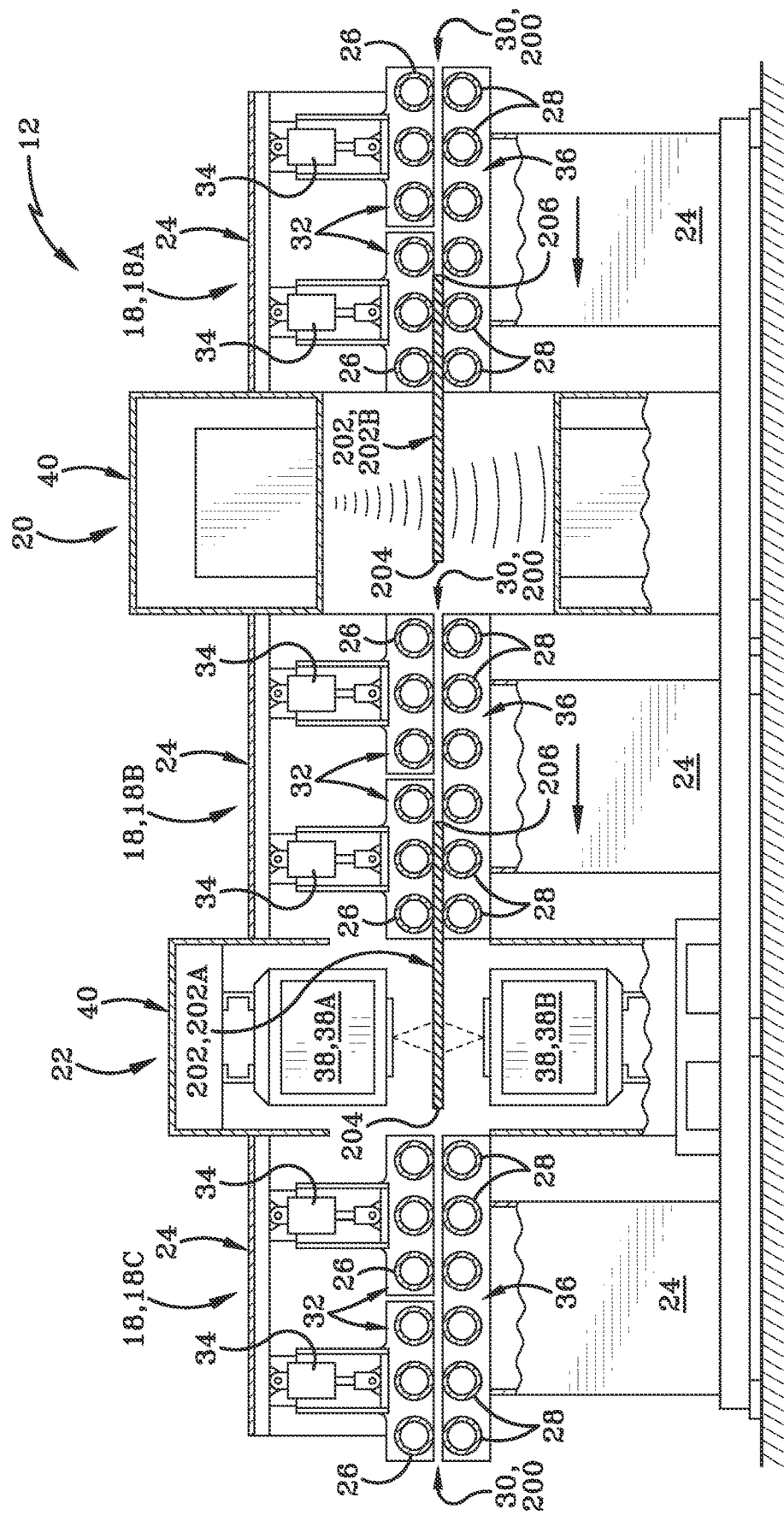
FIG. 19B is a front elevation partial cross section operational view of a scanning unit of the automated inline rip saw system, according to one aspect of the present disclosure.

With reference to FIGS. 19A and 19B, boards 202 may be delivered to rip saw system 10 through any suitable means, including automated feeders, manual feeding, or any other feeding method, or any suitable combination thereof. According to one aspect, boards 202 may be supplied by an automated queueing feeder that can detect, track, and communicate the position of a board 202 to rip saw system 10 as a board 202 approaches the first roller assembly 18A.

A first board 202A may then be inserted into a first roller assembly 18A where one or more sensors in scanning unit 12 May detect the presence and position of the first board 202A. As rip saw system 10 can track the position of a board 202, it can various components, for example, scanners 20 and 22 and roller assemblies 18, to prepare and/or take an action in response to the presence of a board 202. Such reactive responses may include powering on, tracking, or the like. In addition, first roller assembly 18A may move upper roller sets 32 down into position wherein one or more upper rollers 26 may contact the top surface 212 of the first board 202A.

This arrangement may allow for boards 202 of varying thickness to be securely moved through scanning unit 12 while being held steady by upper rollers 26. As first board 202A moves through the first roller assembly 18A, upper roller sets can retract once the board 202A passes.

Next, the first board 202A may be moved into the first scanner 20. Where first scanner 20 is an x-ray scanner, first board 202A may be x-rayed for internal structure to identify density variation therein, which may be indicative of one or more flaws in the board 202A. As the first board 202A is scanned, image data may be collected and evaluated to locate any flaws or features in the board 202A and these findings may be transmitted on to skewing unit 14 and cutting unit 16.

First end 204 of board 202A may then move into the second roller assembly 18B while the first scanner 20 continues scanning the second end 206 of first board 202A. As the first board 202A continues to move through second roller assembly 18B, the first end 204 thereof will move into the second scanner 22. Where second scanner 22 is an optical scanner, first board 202A may then be scanned for surface imperfections, variations, or other such features. This optical scan may reveal additional items that did not show up or were otherwise undetected by the first scanner 20, but may further confirm the features that were detected by the first scanner 20, provided those features show on an exterior surface of the board 202.

As first board 202A continues to move down path 200 though second roller assembly 18B and second scanner 22, a second board 202B can be prepared and delivered into the first roller assembly 18A, as best seen in FIG. 19B. Thus, while second scanner 22 is scanning the first board 202A, the first scanner 20 can be simultaneously scanning the second board 202B. Subsequent boards 202 may be fed into system 10 on a continuous or semi-continuous basis, with a minimal gap between boards 202.

Continuing in the same fashion, first board 202A may then move into third roller assembly 18C and towards skewing unit 14 while second board 202B moves through first scanner 20 and into second roller assembly 18B.

Figure 20:
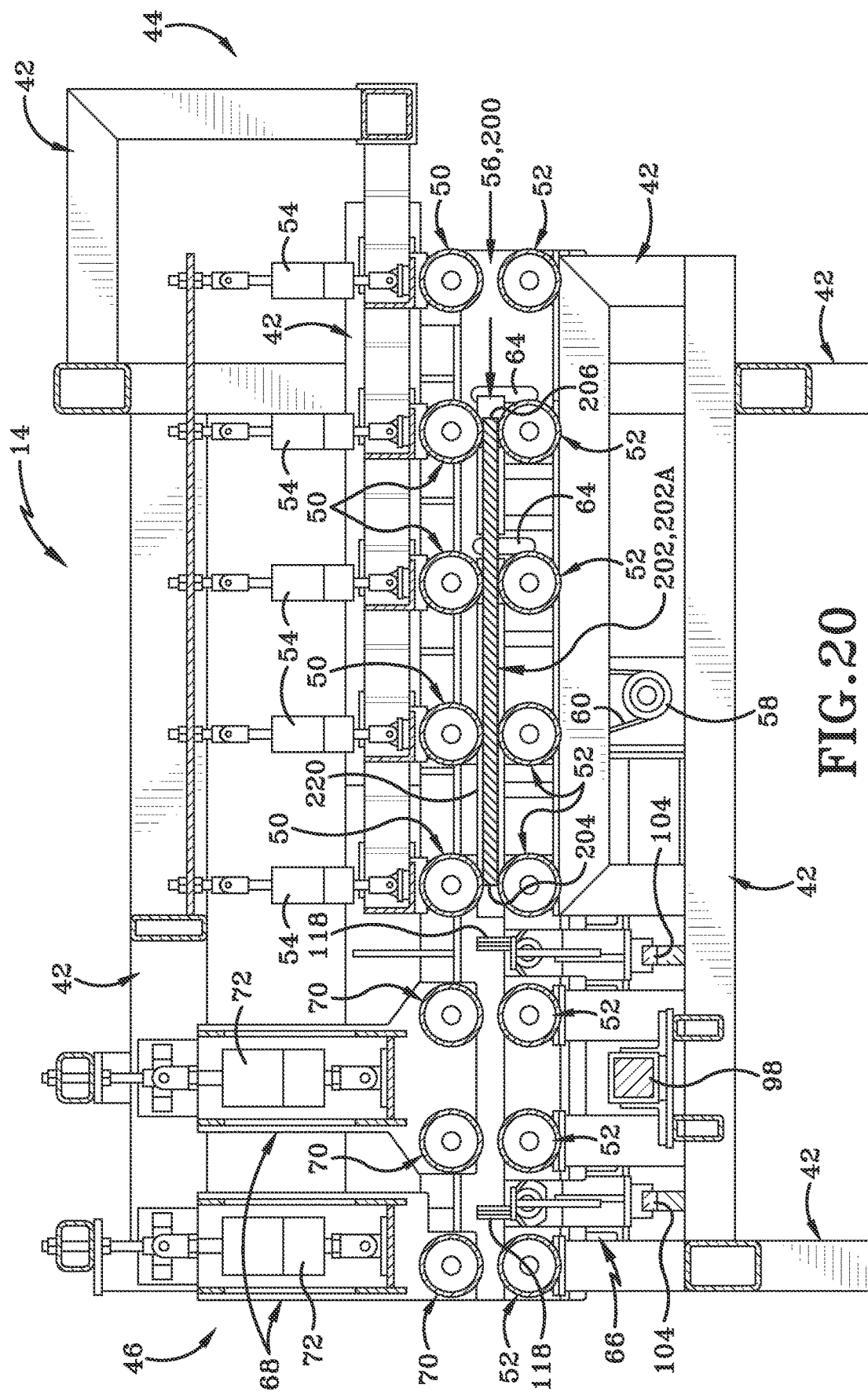
FIG. 20 is a front elevation partial cross section operational view of a skewing unit of the automated inline rip saw system, according to one aspect of the present disclosure.

With reference now to FIGS. 20-21D, the operation of skewing unit 14 will now be discussed. FIG. 20 shows a side elevation view of first board 202A moving down path 200 through skewing unit 14. As discussed herein, the skewing assembly 66 may be located towards the second end 46 of skewing unit 14. Accordingly, as first board 202A moves into skewing unit 14 at the first end 44 thereof, the operation is substantially similar to the roller assemblies 18 of scanning unit 12. In particular, upper rollers 50 may be lowered to contact the top surface 212 of the first board 202A. while upper and lower rollers 50 and 52 move first board 202A towards and into skewing assembly 66.

Figure 21A:
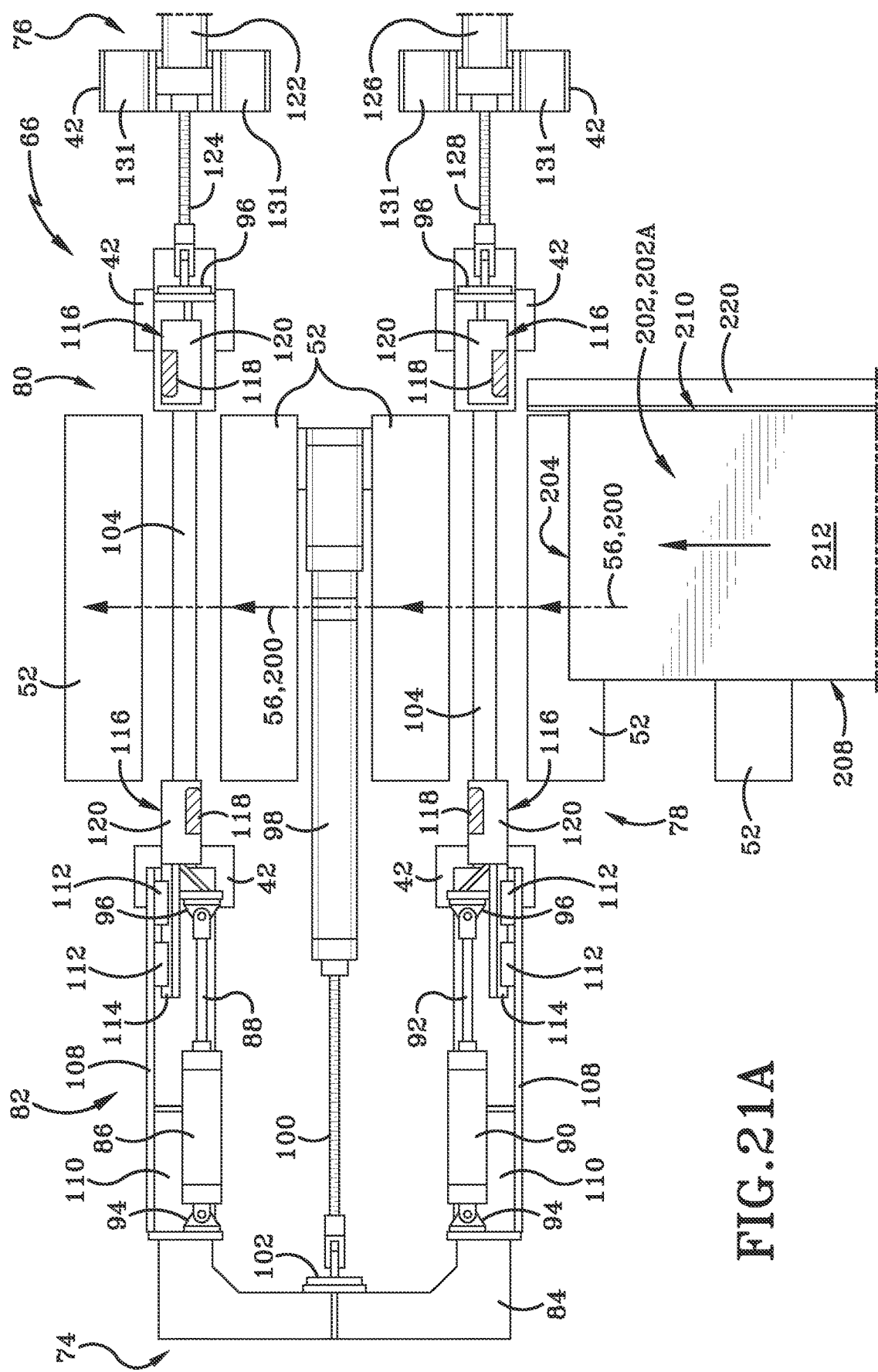
FIG. 21A is an operational view of a skewing assembly, according to one aspect of the present disclosure.

With reference to FIGS. 21A-21D, first board 202A is shown in an overhead view as it moves through and is skewed by skewing assembly 66. As seen in FIG. 21A, first board 202A may be guided into skewing assembly 66 by a guide rail 220. Guide rail 220 may contact second side 210 of first board 202A to align the second side 210 with the skewing pins 118 on the fixed second side 76 of skewing assembly 66. Since the third and fourth skewing actuators 122 and 126 on the second side 76 of skewing assembly 66 are fixed to the frame 42, the skewing pins 118 on that side may serve as an alignment reference point to ensure first board 202A is properly positioned within skewing assembly 66. At this point, first board 202A has not entered the skewing assembly 66, so the sled 84 is moved away from board 202A to allow clearance therefor.

Figure 21B:
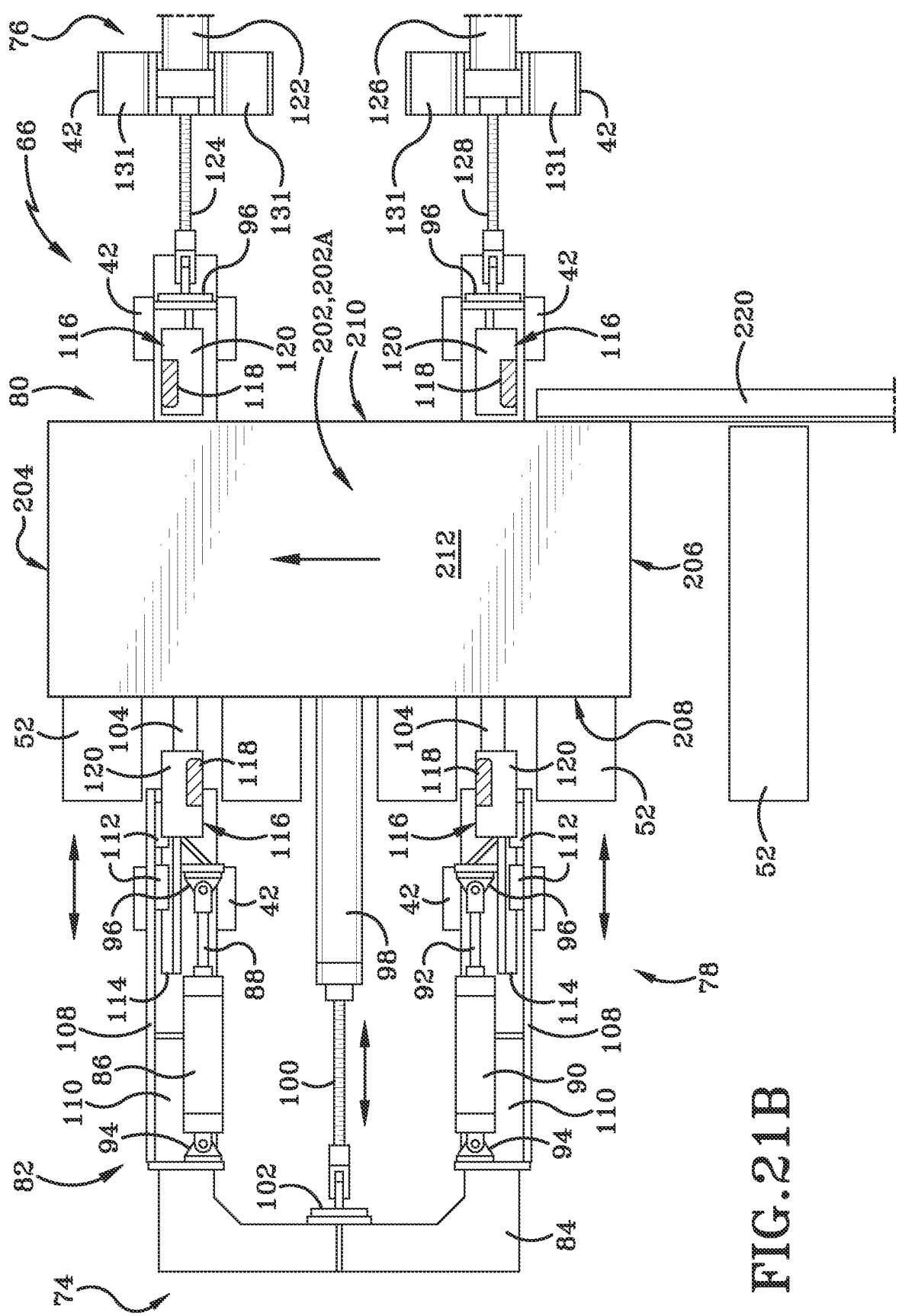
FIG. 21B is an operational view of a skewing assembly, according to one aspect of the present disclosure.

With reference now to FIG. 21B, as first board 202A moves into skewing assembly 66, sled 84 may move towards first board 202A by operation of coarse adjustment actuator 98 and piston 100. This will draw skewing pins 118 of first and second skewing actuators 86 and 90 into close proximity with first side 208 of first board 202A. Simultaneously, or in rapid succession, first through fourth skewing actuators 86, 90, 122, and 126 may extend the respective pistons 88, 92, 124, and 128 to bring skewing pins 118 into contact with first and second sides 208 and 210 of first board 202A. At this point, board 202A is held in place momentarily by all four skewing pins 118 on the sides, and by skewing rollers 70 on the top surface 212 and lower rollers 52 on the bottom. In actual operation, these actions occur in fractions of a second as rip saw system 10 may be operable to scan, skew, and cut as many as approximately 60-70 boards 202 per minute, as discussed further herein.

Figure 21C:
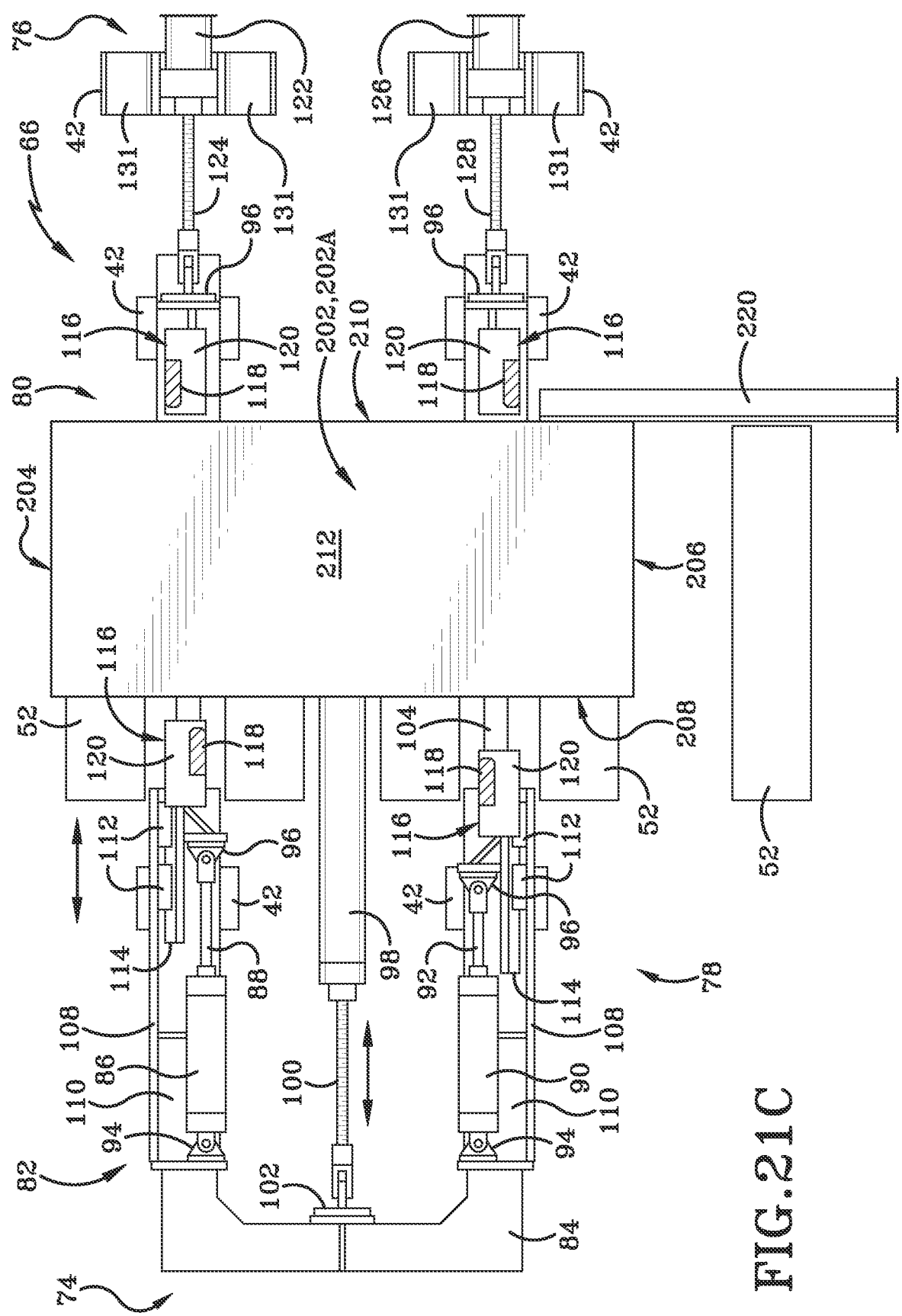
FIG. 21C is an operational view of a skewing assembly, according to one aspect of the present disclosure.

With reference to FIG. 21C-21D, as skewing pins 118 come into contact with sides 208 and 210 of first board 202A, skewing pistons 88, 92, 124, and 128 may be extended or retracted to skew first board 202A relative to the longitudinal axis defined by path 200. This skewing amount may and will vary for each board 202 processed as the location and type of cuts to be made in each board 200 are not identical. The amount or degree to which a board 202 may be skewed may be determined by the data previously collected by first and second scanners 20 and 22.

The act of skewing a board 202 itself is performed with one of the four skewing pins 118 serving as a fixed reference point, which, once determined, will remain the same for all boards 202 processed by rip saw system 10 in a given production run. Put another way, while the reference point may be defined by any of the four skewing pins 118, once an individual skewing pin 118 is selected, it remains the reference point and does not change on a board to board basis. Instead, it may be changed between runs, but it is not necessary to do so. This fixed reference point helps facilitate consistent and precise skewing of each board 202 being processed by rip saw system 10.

Once the first board 202A is skewed to the desired position, the skewing pistons 88, 92, 124, and 128 may be retracted and sled 84 may be moved away from first board 202A to allow clearance for first board 202A to be moved out of skewing unit 14 and towards cutting unit 16 and to allow second board 202B to enter the skewing assembly 66.

With reference to FIGS. 22-24C, first board 202A is shown in an overhead view as it moves through and is cut within cutting unit 16. As mentioned previously herein, cutting unit 16 may include multiple saw assemblies 142 having multiple saw blades 162. In particular, as shown and described herein, each saw assembly 142 may have a pair of saw blades 162 with each blade 162 having its own dedicated arbor motor 166. Each blade 162 may therefore be operated and move independently of all other blades 162 within cutting unit 16. Further, every blade 162 may be provided as any suitable blade type. As shown in FIGS. 22-24C, six blades 162 are used and described; however, it will be reiterated that any suitable number of blades 162 can be used, as desired, and cutting unit 16 may be scaled according to the desired implementation.

Figure 22:
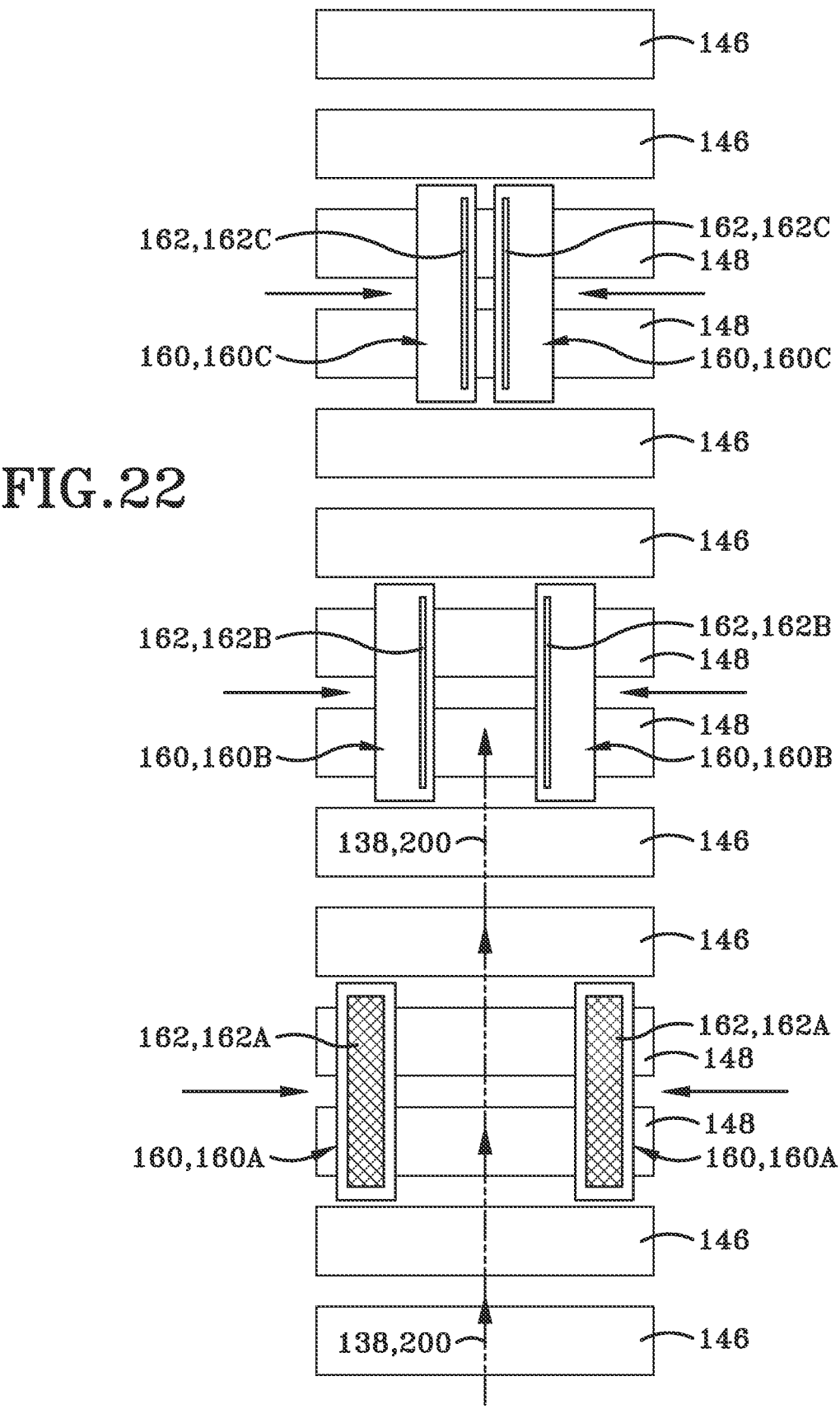
FIG. 22 is an operational view of a cutting unit, according to one aspect of the present disclosure.

With reference to FIG. 22, saw blades 162 may be aligned according to the scan data collected from scanners 20 and 22, which may dictate which portions of first board 202A are to be removed and where the cuts should be made. Where, as in this example, the first saw blades 162 (shown as 162A) may be hogging blades while second and third blades, 162B and 162C, respectively, may be cutting blades. According to one aspect, in order to prevent mis-cut sections or misaligned portions of the board 202, blades 162 may be moved into position to work from the outside edges 208 and 210 of a board 202 towards the center thereof, such that each cut is progressively closer to the midline of path 200. Where blades 162 are arranged in pairs, the blades 162 may be moved to parallel and narrower positions as a board 202 is moved down path 200.

Figure 23A:
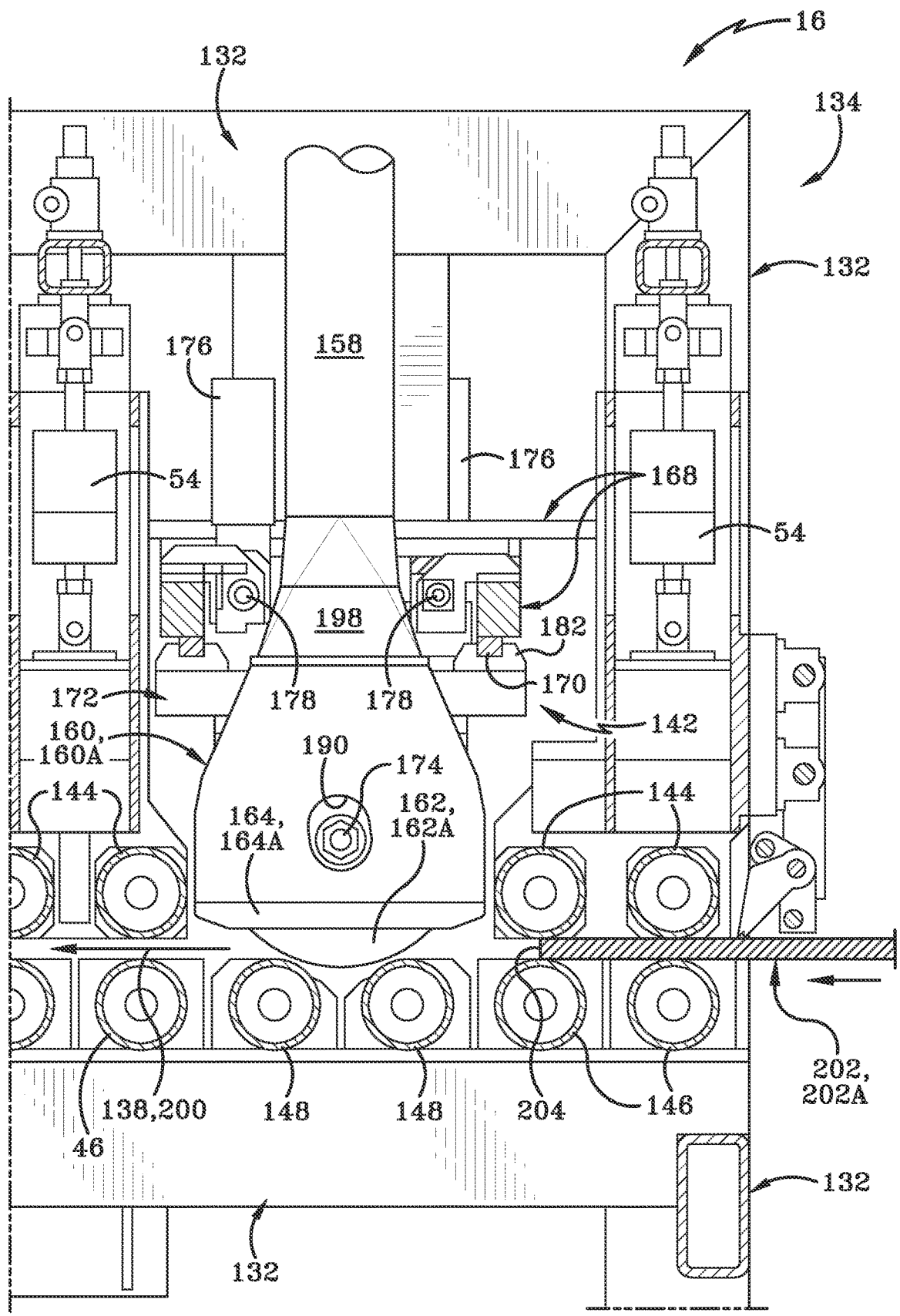
FIG. 23A is a front elevation cross section operational view of a cutting unit of an automated inline rip saw system, according to one aspect of the present disclosure.
Figure 23B:
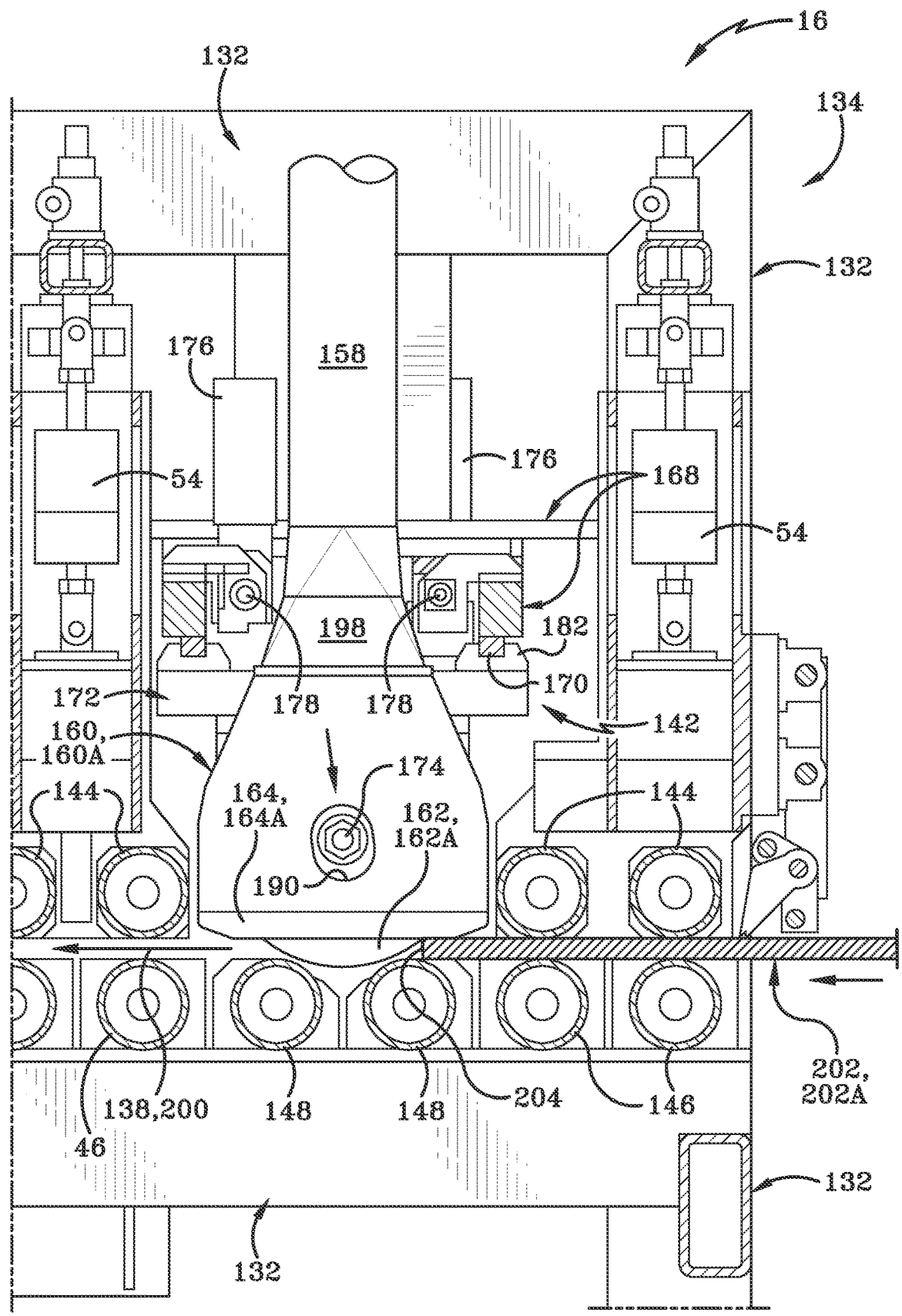
FIG. 23B is a front elevation cross section operational view of a cutting unit of an automated inline rip saw system, according to one aspect of the present disclosure.

With reference to FIG. 23A, as first board 202A then moves into the cutting unit 16 and towards the first saw blades 162A, the first dust hood 160A and foot 164A associated with first blades 162A may be in an upward or raised position to allow first board 202A sufficient clearance. As shown in FIG. 23B, as first board 202A then approaches the blade 162A, first hood 160A and foot 164A may be moved into a lowered position such that the foot 164A contacts the top surface 212 of first board 202A. This contact may facilitate a cleaner and more precise cut as light pressure may be applied to first board 202A by hood 160A and foot 164A to help prevent kickback or other movement of board 202A during the cutting process. Simultaneously, hood 160A, which may be operationally connected to a dust removal vacuum system via conduit 158 and coupling sleeve 198, may serve to vacuum or otherwise remove cut portions of board 202A and the saw dust created from the cutting process from the cutting unit 16.

As first board 202A moves through the cutting unit 16, once it is clear of the first saw blades 162A, the first hood 160A may be moved back to the raised position, which may trigger a signal to the other units of rip saw system 10 that cutting unit 16 is ready for the next board 202B. This may also provide a momentary break in operation to allow first saw blades 162A to reset and move into the next position for the next board 202B. This process may repeat for all saw blades 162 and hoods 160 as discussed further below.

Figure 24A:
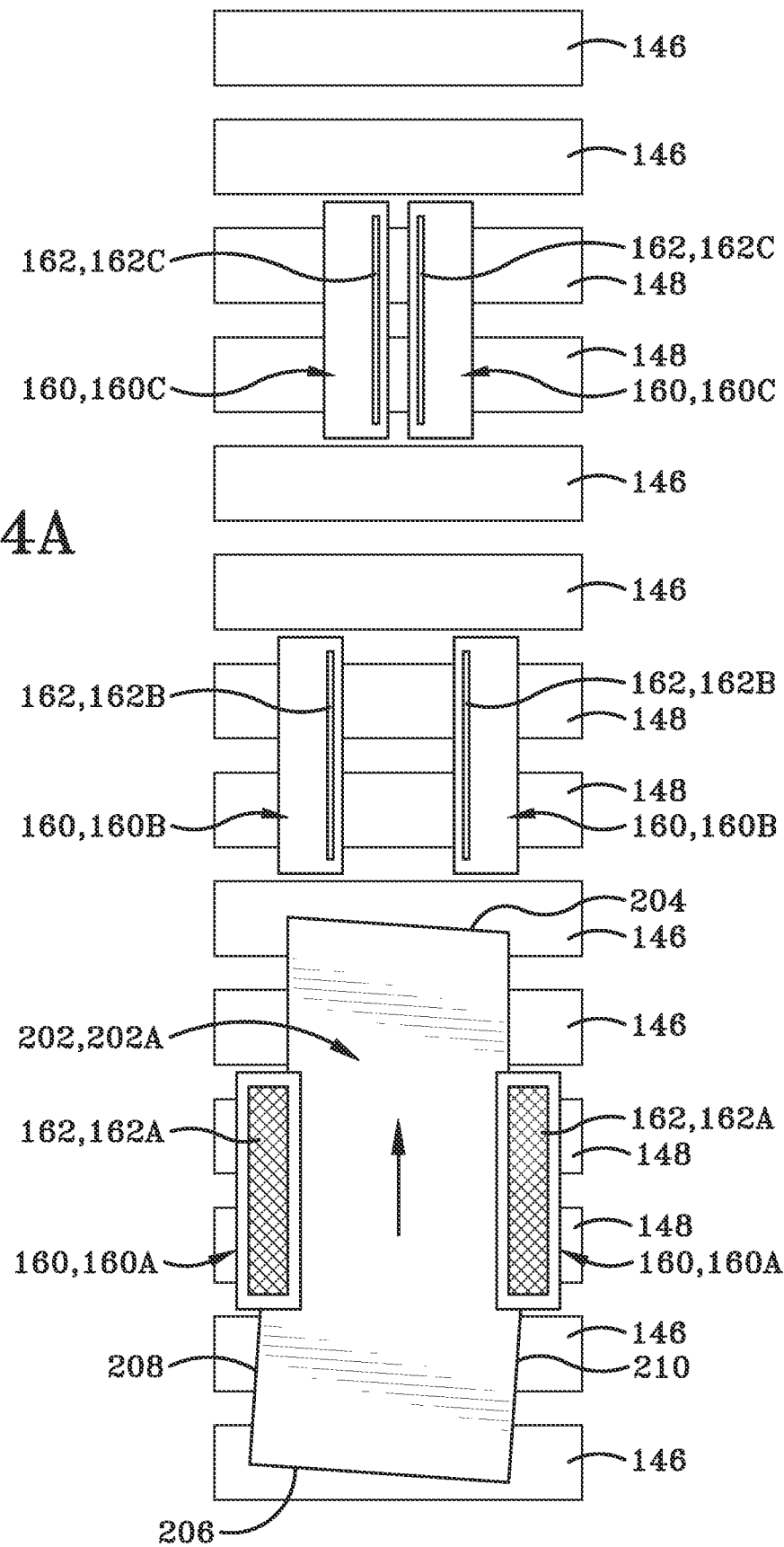
FIG. 24A is an operational view of a cutting unit, according to one aspect of the present disclosure.
Figure 24B:
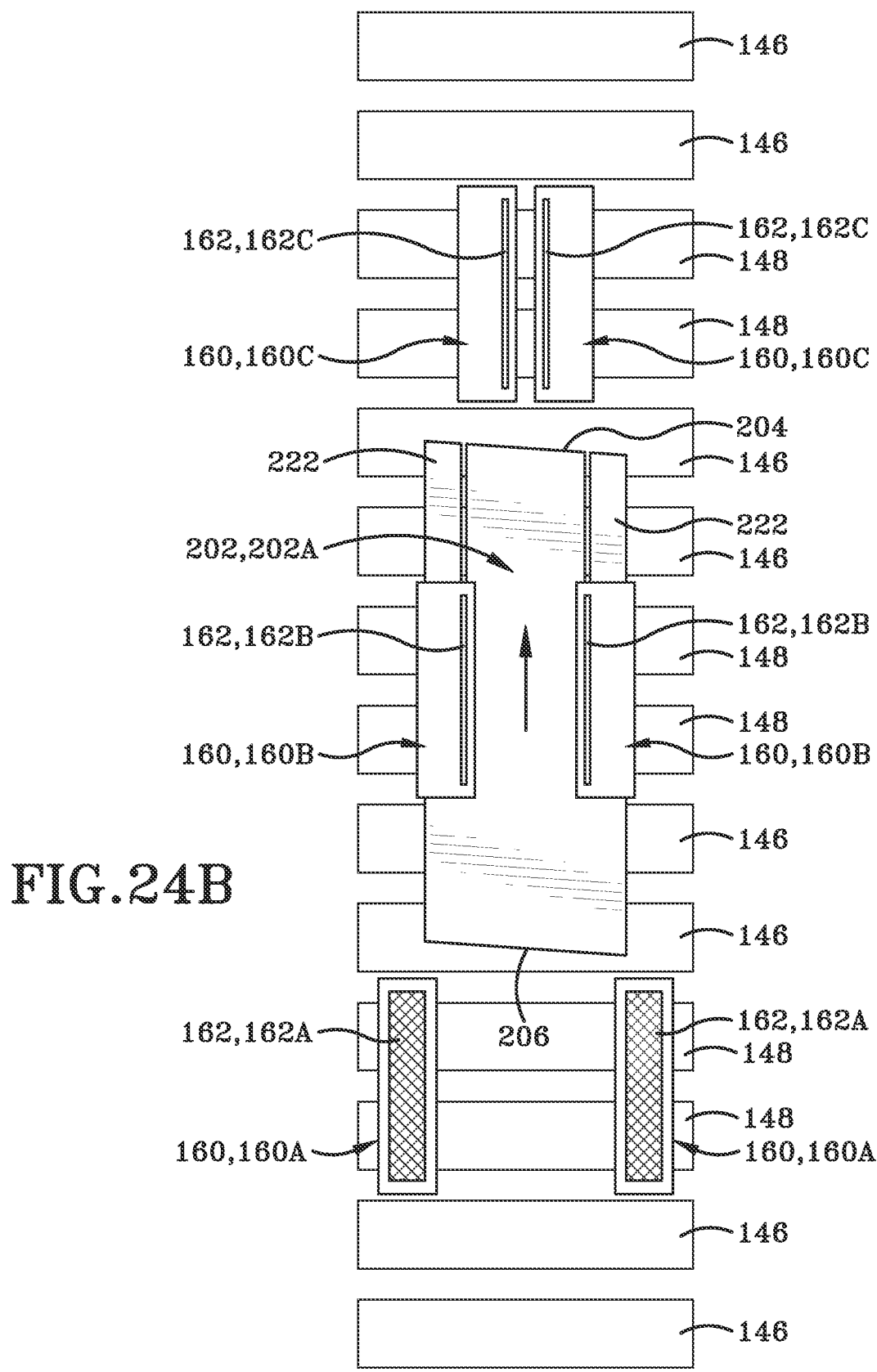
FIG. 24B is an operational view of a cutting unit, according to one aspect of the present disclosure.
Figure 24C:
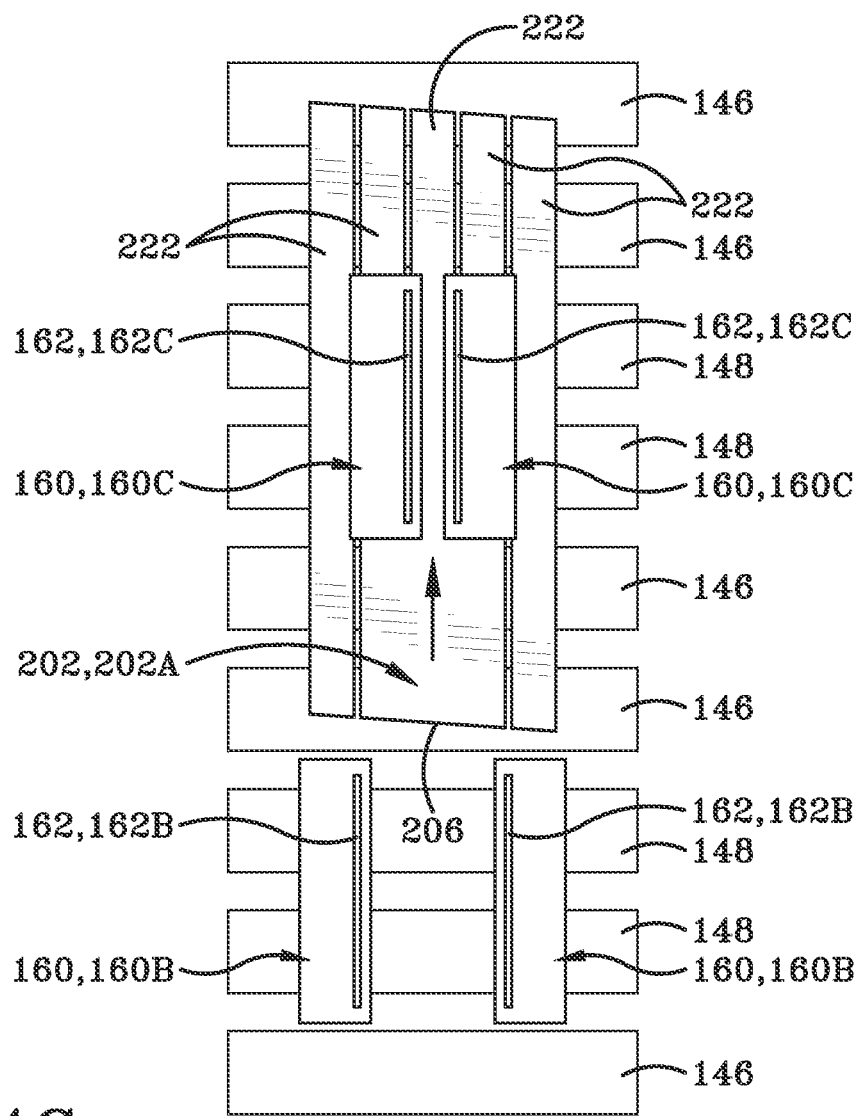
FIG. 24C is an operational view of a cutting unit, according to one aspect of the present disclosure.
Figure 24C:
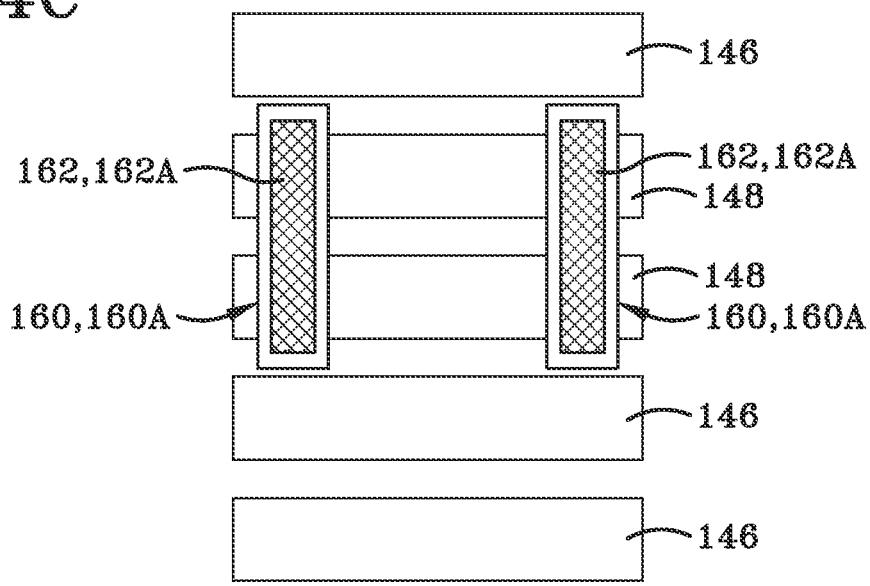

With reference to FIGS. 24A-24C, as first board 202A moves through cutting unit 16, it will be cut down to the determined size and defects may be removed therefrom. For example, the edges, which may be sapwood 218, may be hogged and removed (FIG. 24A) by first saw blades 162A. Then, second saw blades 162B may make a cut through board 202A to trim the board 202A or to otherwise remove a portion of the board 202A (FIG. 24B). Then, third saw blades 162C may make a second cut through the board 202A to trim the board 202A further, or to remove additional portions of the board 202A, as desired (FIG. 24C). As shown, board 202A may be cut into staves 222. Alternatively, boards 202 processed through rip saw system 10 may be cut and utilized for any suitable purpose.

As described herein, rip saw system 10 may process multiple boards 202 in rapid succession, reaching averages of nearly 60-70 boards per minute. According to one aspect, this is enabled by the ability of rip saw system 10 to simultaneously scan, skew, and cut boards. For example, reference has been made herein to first board 202A and second board 202B; however, rip saw system 10 may handle a third board and fourth board (not shown) simultaneously. In particular, rip saw system 10 may be actively cutting first board 202A, while skewing second board 202B, optically scanning a third board with second scanner 22, and x-raying a fourth board with first scanner 20. When connected to an automated feeding system, boards 202 may be fed into rip saw system 10 on a continuous or semi-continuous basis. Further, the elimination of secondary queues between the scanning unit 12 and skewing unit 14, and between the skewing unit 14 and cutting unit 16 can allow for faster processing of boards through rip saw system 10 with fewer errors or interruptions as boards 202 are scanned and processed on a near real-time scale.

One key element and advantage provided by rip saw system 10 is the ability to detect and remove sapwood 218. In particular, as discussed previously herein, present systems often process wood in a dry state, i.e. after it has been milled and dried. Often this wood may sit for days or weeks between stages, and is not usually scanned or cut to size until late in the process. At this point, sapwood 218 is difficult to reliably detect as the drying process tends to darken sapwood 218 in both optical scans and x-rays, making it hard to distinguish from surrounding heartwood. Accordingly, present systems tend to produce lower usable yields and further tend to produce wood products with a higher chance of flaws or defects included therein. In certain industries, particularly the barrel stave industry, the end product can suffer if too many flaws are included, or is too much sapwood 218 is left behind. Specifically, barrel staves that are used in making, distilling, storing, and/or aging spirits have a low tolerance for such flaws as the inclusion thereof tends to lead to seepage or leakage from the barrels which can change the flavor profile, alcohol content, quality, and ultimately the value of the liquor in the barrel. Thus, when processing wood for barrel staves, current systems tend to over-process the staves, leading to more waste, a lower yield of usable wood, and a higher cost.

With reference to FIG. 25, rip saw system 10 may be employed much earlier in the wood processing cycle, and the configuration and operation thereof may provide a significantly higher level of precision in barrel stave production, thus reducing waste and cost, while maximizing the usable yields. In particular, rip saw system 10 may scan green lumber, i.e. lumber that is freshly cut, and may detect and remove a higher percentage of sapwood 218 and other flaws without over-processing the wood. As shown in FIG. 25, a tree or stand of trees 224 may be harvested and directed to a milling facility or mill 226. At the mill 226, they may be processed quickly, by first being half sawn, then quarter sawn, and then sawn into slats or boards 202, which may then be immediately transferred into scanning unit 12. The ideal would be to go from the mill 226 to the scanning unit in approximately five minutes or less, but benefits of this early processing may be realized within the first few hours after the trees 224 are half and quarter sawn.

In particular, in green wood, sapwood 218 is significantly lighter in color and more easily and readily identified and removed. By scanning freshly sawn wood, rip saw system 10 is able to more precisely locate and remove sapwood 218. Additionally, having a single saw blade 162 per arbor motor 166 may further provide benefits as cutting green wood itself introduces challenges into a rip saw system. One such challenge is the presence of excess moisture and sap, which is at least partially alleviated by having single saw blades 162 with dedicated motors 166 which may provide less opportunity for moisture and sap to collect and cause issues in the processing.

Further, the sliding arrangement of mounting sleds 172 in saw assemblies 142 allows for fast, safe, and easy access to saw blades 162 and to the other components of saw assemblies 142 for cleaning and maintenance thereof. This may likewise reduce the effect of excess moisture and sap within rip saw system 10 as it can be more readily removed or cleaned.

Although shown and described herein as a rip saw system 10, additional elements or components may be provided or otherwise utilized in conjunction therewith. By way of one non limiting example, a crosscut saw unit may be provided downstream of the cutting unit 16 for additional cuts to finished boards. According to another example, as mentioned herein, automated feeding or material handling systems may be employed at either end of rip saw system 10 to feed or remove boards 202 and/or staves 222 into or from rip saw system 10.

Various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

The above-described embodiments can be implemented in any of numerous ways. For example, embodiments of technology disclosed herein may be implemented using hardware, software, or a combination thereof. When implemented in software, the software code or instructions can be executed on any suitable processor or collection of processors, whether provided in a single computer or distributed among multiple computers. Furthermore, the instructions or software code can be stored in at least one non-transitory computer readable storage medium.

Also, a computer or smartphone utilized to execute the software code or instructions via its processors may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computer may receive input information through speech recognition or in other audible format.

Such computers or smartphones may be interconnected by one or more networks in any suitable form, including a local area network or a wide area network, such as an enterprise network, and intelligent network (IN) or the Internet. Such networks may be based on any suitable technology and may operate according to any suitable protocol and may include wireless networks, wired networks or fiber optic networks.

The various methods or processes outlined herein may be coded as software/instructions that is executable on one or more processors that employ any one of a variety of operating systems or platforms. Additionally, such software may be written using any of a number of suitable programming languages and/or programming or scripting tools, and also may be compiled as executable machine language code or intermediate code that is executed on a framework or virtual machine.

In this respect, various inventive concepts may be embodied as a computer readable storage medium (or multiple computer readable storage media) (e.g., a computer memory, one or more floppy discs, compact discs, optical discs, magnetic tapes, flash memories, USB flash drives, SD cards, circuit configurations in Field Programmable Gate Arrays or other semiconductor devices, or other non-transitory medium or tangible computer storage medium) encoded with one or more programs that, when executed on one or more computers or other processors, perform methods that implement the various embodiments of the disclosure discussed above. The computer readable medium or media can be transportable, such that the program or programs stored thereon can be loaded onto one or more different computers or other processors to implement various aspects of the present disclosure as discussed above.

The terms "program" or "software" or "instructions" are used herein in a generic sense to refer to any type of computer code or set of computer-executable instructions that can be employed to program a computer or other processor to implement various aspects of embodiments as discussed above. Additionally, it should be appreciated that according to one aspect, one or more computer programs that when executed perform methods of the present disclosure need not reside on a single computer or processor, but may be distributed in a modular fashion amongst a number of different computers or processors to implement various aspects of the present disclosure.

Computer-executable instructions may be in many forms, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that convey relationship between the fields. However, any suitable mechanism may be used to establish a relationship between information in fields of a data structure, including through the use of pointers, tags or other mechanisms that establish relationship between data elements.

All definitions, as defined and used herein, should be understood to control over dictionary definitions, definitions in documents incorporated by reference, and/or ordinary meanings of the defined terms.

"Logic", as used herein, includes but is not limited to hardware, firmware, software, and/or combinations of each to perform a function(s) or an action(s), and/or to cause a function or action from another logic, method, and/or system. For example, based on a desired application or needs, logic may include a software controlled microprocessor, discrete logic like a processor (e.g., microprocessor), an application specific integrated circuit (ASIC), a programmed logic device, a memory device containing instructions, an electric device having a memory, or the like. Logic may include one or more gates, combinations of gates, or other circuit components. Logic may also be fully embodied as software. Where multiple logics are described, it may be possible to incorporate the multiple logics into one physical logic. Similarly, where a single logic is described, it may be possible to distribute that single logic between multiple physical logics.

Furthermore, the logic(s) presented herein for accomplishing various methods of this system may be directed towards improvements in existing computer-centric or internet-centric technology that may not have previous analog versions. The logic(s) may provide specific functionality directly related to structure that addresses and resolves some problems identified herein. The logic(s) may also provide significantly more advantages to solve these problems by providing an exemplary inventive concept as specific logic structure and concordant functionality of the method and system. Furthermore, the logic(s) may also provide specific computer implemented rules that improve on existing technological processes. The logic(s) provided herein extends beyond merely gathering data, analyzing the information, and displaying the results. Further, portions or all of the present disclosure may rely on underlying equations that are derived from the specific arrangement of the equipment or components as recited herein. Thus, portions of the present disclosure as it relates to the specific arrangement of the components are not directed to abstract ideas. Furthermore, the present disclosure and the appended claims present teachings that involve more than performance of well-understood, routine, and conventional activities previously known to the industry. In some of the method or process of the present disclosure, which may incorporate some aspects of natural phenomenon, the process or method steps are additional features that are new and useful.

The articles "a" and "an," as used herein in the specification and in the claims, unless clearly indicated to the contrary, should be understood to mean "at least one." The phrase "and/or," as used herein in the specification and in the claims (if at all), should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc. As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Spatially relative terms, such as "under", "below", "lower", "over", "upper", "above", "behind", "in front of", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal", "lateral", "transverse", "longitudinal", and the like are used herein for the purpose of explanation only unless specifically indicated otherwise.

Although the terms "first" and "second" may be used herein to describe various features/elements, these features/elements should not be limited by these terms, unless the context indicates otherwise. These terms may be used to distinguish one feature/element from another feature/element. Thus, a first feature/element discussed herein could be termed a second feature/element, and similarly, a second feature/element discussed herein could be termed a first feature/element without departing from the teachings of the present invention.

An embodiment is an implementation or example of the present disclosure. Reference in the specification to "an embodiment," "one embodiment," "some embodiments," "one particular embodiment," "an exemplary embodiment," or "other embodiments," or the like, means that a particular feature, structure, or characteristic described in connection with the embodiments is included in at least some embodiments, but not necessarily all embodiments, of the invention. The various appearances "an embodiment," "one embodiment," "some embodiments," "one particular embodiment," "an exemplary embodiment," or "other embodiments," or the like, are not necessarily all referring to the same embodiments.

If this specification states a component, feature, structure, or characteristic "may", "might", or "could" be included, that particular component, feature, structure, or characteristic is not required to be included. If the specification or claim refers to "a" or "an" element, that does not mean there is only one of the element. If the specification or claims refer to "an additional" element, that does not preclude there being more than one of the additional element.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range recited herein is intended to include all sub-ranges subsumed therein.

Additionally, the method of performing the present disclosure may occur in a sequence different than those described herein. Accordingly, no sequence of the method should be read as a limitation unless explicitly stated. It is recognizable that performing some of the steps of the method in a different order could achieve a similar result.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively.

In the foregoing description, certain terms have been used for brevity, clearness, and understanding. No unnecessary limitations are to be implied therefrom beyond the requirement of the prior art because such terms are used for descriptive purposes and are intended to be broadly construed.

Moreover, the description and illustration of various embodiments of the disclosure are examples and the disclosure is not limited to the exact details shown or described.

The invention claimed is:

1. An automated rip saw system comprising:
   a first scanner operable to scan a piece of wood with x-rays;
   a second scanner operable to optically scan the piece of wood;
   a skewing unit operable to skew the piece of wood, the skewing unit comprising:
      a plurality of rollers operable to move the piece of wood through the skewing unit; and
      a skewing assembly having at least one skewing pin operable to interact with a first side of the piece of wood and at least one skewing pin operable to interact with a second side of the piece of wood;
   a cutting unit having at least one saw assembly therein operable to cut the piece of wood; and
   a continuous path defined through the first scanner, the second scanner, the skewing unit, and the cutting unit;
   wherein the piece of wood is skewed by the skewing unit to an angle relative to the path such that the at least one saw assembly of the cutting unit is aligned with the piece of wood to remove one or more of a knot, a ray, and an area of sapwood detected by at least one of the first and second scanners.

2. The saw system of claim 1 further comprising:
   at least one roller assembly operable to move the piece of wood down the path from the first scanner to the second scanner;
   at least one roller operable to move the piece of wood from the second scanner to the skewing unit; and
   at least one roller operable to move the piece of wood from the skewing unit to the at least one saw assembly.

3. The saw system of claim 1 wherein the skewing assembly further comprises:
   a coarse adjustment actuator and piston assembly;
   at least one skewing actuator and piston assembly carrying the at least one skewing pin on the first side of the piece of wood and in operable connection with the coarse adjustment actuator and piston assembly; and
   at least one additional skewing actuator and piston assembly carrying the at least one skewing pin on the second side of the piece of wood.

4. The saw system of claim 3 wherein the skewing assembly further comprises:
   a sled carrying the at least one skewing actuator and piston assembly on the first side of the piece of wood thereon;
   wherein the coarse adjustment actuator and piston assembly is operable to move the sled so that the at least one skewing actuator and piston assembly is in contact with the first side of the piece of wood.

5. The saw system of claim 4 wherein the at least one skewing actuator and piston assembly on the first side of the piece of wood and the at least one additional skewing actuator and piston assembly on the second side of the piece of wood are operable to skew the piece of wood.

6. The saw system of claim 1 wherein the saw assembly further comprises:
   a first saw blade having a first dedicated arbor motor operably connected thereto;
   a second saw blade having a second dedicated arbor motor operably connected thereto;
   a frame having at least one rail;
   a first mounting sled engaged with the at least one rail of the frame and carrying the first saw blade and first arbor motor thereon; and
   a second mounting sled engaged with the at least one rail of the frame and carrying the second saw blade and second arbor motor thereon.

7. The saw system of claim 6 further comprising:
   at least one slider slidably engaged between the first mounting sled and the at least one rail; and
   at least one additional slider slidably engaged between the second mounting sled and the at least one rail.

8. The saw system of claim 7 wherein the first and second mounting sleds are transversely moveable along the at least one rail of the frame relative to the path defined through the cutting unit to place the first and second saw blades into the path to cut the piece of wood.

9. The saw system of claim 8 further comprising:
   a first dust hood at least partially enclosing the first saw blade therein; and
   a second dust hood at least partially enclosing the second saw blade therein.

10. The saw system of claim 9 wherein the first and second dust hoods are vertically movable relative to the first and second saw blades.

11. The saw system of claim 10 further comprising:
    a first foot on the first dust hood; and
    a second foot on the second dust hood; wherein the first and second feet are operable to secure the piece of wood while being cut.

12. The saw system of claim 1 wherein the saw system is operable to simultaneously cut a first piece of wood with the saw assembly; skew a second piece of wood with the skewing unit; optically scan a third piece of wood with the second scanner; and x-ray scan a fourth piece of wood with the first scanner.

13. A method of cutting a piece of wood comprising:
    inserting a piece of wood into a first scanner of a rip saw system;
    performing an x-ray scan of the piece of wood with the first scanner;
    moving the piece of wood from the first scanner to a second scanner with at least one roller assembly;
    performing an optical scan of the piece of wood with the second scanner;
    detecting and identifying at least one flaw in the piece of wood;
    moving the piece of wood from the second scanner to a skewing unit, the skewing unit comprising:
       a plurality of rollers operable to move the piece of wood through the skewing unit; and
       a skewing assembly having at least one skewing pin operable to interact with a first side of the piece of wood and at least one skewing pin operable to interact with a second side of the piece of wood;
    skewing the piece of wood relative to a path defined through the first scanner, the second scanner, and the skewing unit;

moving the skewed piece of wood from the skewing unit to a cutting unit having at least one saw assembly therein; and cutting the piece of wood with the at least one saw assembly to remove the at least one flaw therefrom.

14. The method of claim 13 detecting and identifying the at least one flaw further comprises:

detecting at least one of a knot, a ray, and an area of sapwood in the piece of wood.

15. The method of claim 13 wherein skewing the piece of wood further comprises:

engaging a first side of the piece of wood with a first skewing actuator and piston assembly and a second skewing actuator and piston assembly;

engaging a second side of the piece of wood with a third skewing actuator and piston assembly and a fourth skewing actuator and piston assembly;

moving at least one of the first, second, third, and fourth skewing actuator and piston assemblies; and rotating the piece of wood relative to the path.

16. The method of claim 13 wherein cutting the piece of wood further comprises:

moving a first saw blade having a first dedicated arbor motor operably connected thereto into the path;

moving a second saw blade having a second dedicated arbor motor operably connected thereto into the path;

directing the piece of wood to the first and second saw blades;

securing the piece of wood with a first foot of a first dust hood in operable connection to the first saw blade and a second foot of a second dust hood in operable connection to the second saw blade; and cutting the piece of wood with at least one of the first and second saw blades.

17. The method of claim 16 further comprising:

moving a third saw blade having a third dedicated arbor motor operably connected thereto into the path behind the first and second saw blades;

moving a fourth saw blade having a fourth dedicated arbor motor operably connected thereto into the path behind the first and second saw blades;

directing the piece of wood to the third and fourth saw blades;

securing the piece of wood with a third foot of a third dust hood in operable connection to the third saw blade and a fourth foot of a fourth dust hood in operable connection to the fourth saw blade; and cutting the piece of wood with at least one of the third and fourth saw blades.

18. The method of claim 13 wherein the rip saw system is operable to simultaneously cut a first piece of wood with the at least one saw assembly; skew a second piece of wood with the skewing unit; optically scan a third piece of wood with the second scanner; and x-ray scan a fourth piece of wood with the first scanner.

19. The method of claim 13 further comprising:

scanning, skewing, and cutting additional pieces of wood to remove detected flaws therefrom on at least a semi-continuous basis.

* * * * *